United States Patent
Kaminski et al.

(10) Patent No.: US 7,781,394 B2
(45) Date of Patent: Aug. 24, 2010

(54) METHODS FOR IDENTIFYING ANTI-TUMOR AND/OR ANTI-ANGIOGENESIS DRUGS WITH DEOXYNUCLEOSIDE 5'-MONOPHOSPHATE N-GLYCOSIDASE AS THE TARGET

(75) Inventors: Pierre Alexandre Kaminski, Paris (FR); Chi Van Dang, Paris Cedex (FR)

(73) Assignees: Institut Pasteur, Paris (FR); Centre National de la Recherche Scientifique, Paris (FR)

( * ) Notice: Subject to any disclaimer, the term of this patent is extended or adjusted under 35 U.S.C. 154(b) by 76 days.

(21) Appl. No.: 11/939,114

(22) Filed: Nov. 13, 2007

(65) Prior Publication Data

US 2008/0276328 A1 Nov. 6, 2008

Related U.S. Application Data

(60) Provisional application No. 60/865,483, filed on Nov. 13, 2006.

(51) Int. Cl.
*A01N 61/00* (2006.01)
*A61K 31/00* (2006.01)
*A61K 49/00* (2006.01)
*G01N 33/00* (2006.01)

(52) U.S. Cl. ................. 514/1; 424/9.1; 800/3
(58) Field of Classification Search ........... None
See application file for complete search history.

(56) References Cited

FOREIGN PATENT DOCUMENTS

WO 03/087312 10/2003

OTHER PUBLICATIONS

McConnell et al., 2003, Molecular and Cellular Biology, 23: 9375-9388.*
Drews, 2000, Science, 287: 1960-1964.*
J. Biol Chem. Mar. 16, 2007;282(11):8150-6. Epub Jan 18, 2007 "The c-Myc Target Gene Rcl (C6orf108) Encodes a Novel Enzyme, Deoxynucleoside 5'-monophosphate N-Glycosidase" Yoan Konto Ghiorghi, et al.
Brian C. Lewis, et al., "Tumor Induction by the c-Myc Target Genes rcl and Lactate Dehydrogenase A[1]" Cancer Research 60, 6178-6183, Nov. 1, 2000.
Brian C. Lewis, et al., "Identification of Putative c-Myc-Responsive Genes: Characterization of rcl, a Novel Growth-Related Gene", Molecular and Cellular Biology, Sep. 1997, p. 4967-4978.
Shin-ichi Akiyama, "The Role of Thymidine Phosphorylase, an Angiogenic Enzyme, in Tumor Progression", Cancer Sci, Nov. 2004, vol. 95, No. 11, pp. 851-857.

* cited by examiner

*Primary Examiner*—Joanne Hama
(74) *Attorney, Agent, or Firm*—Oblon, Spivak, McClelland, Maier & Neustadt, L.L.P.

(57) ABSTRACT

The present invention relates to a novel target for identifying and/or screening antitumor and/or antiangiogenesis agents using the rcl encoded deoxynucleoside 5'monophosphate N-glycosidase.

31 Claims, 8 Drawing Sheets

FIG 1
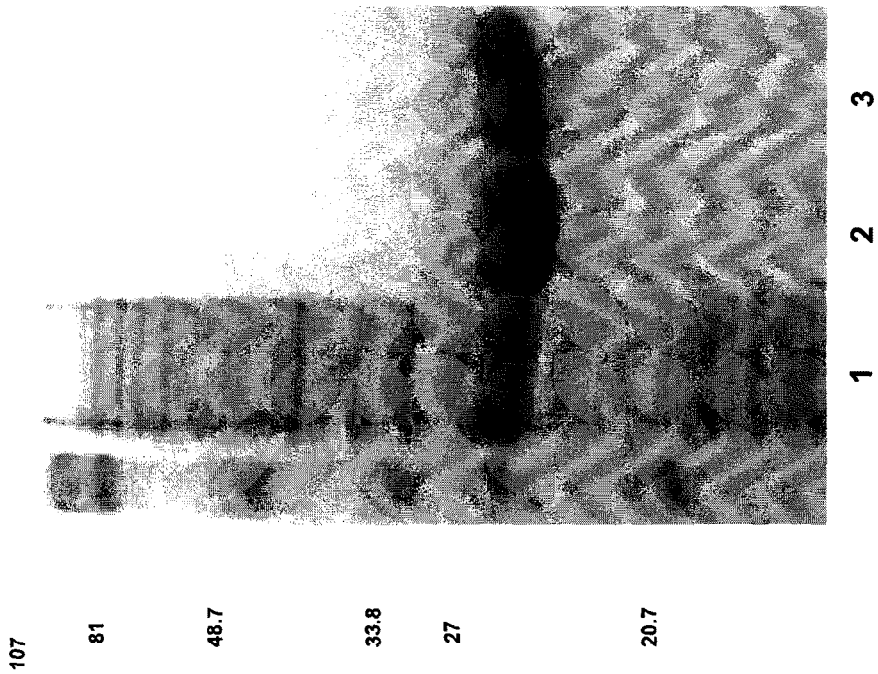
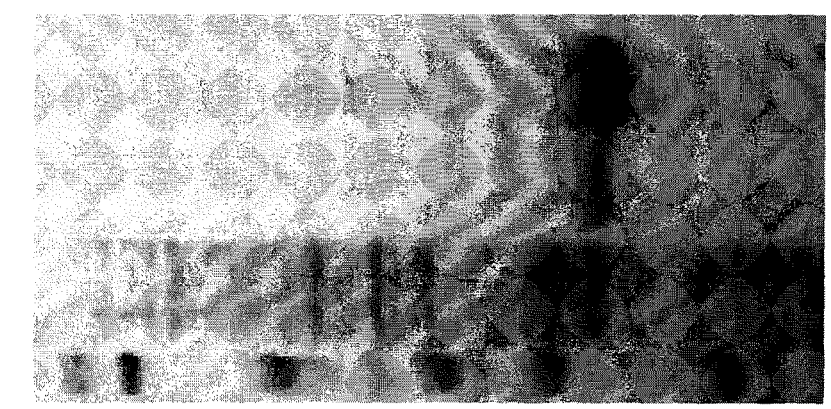

FIG. 3

```
                       10        20        30        40        50        60        70        80
              ....|....*....|....*....|....*....|....*....|....*....|....*....|....*....|....*....|
consensus   1 IYLAGPFFFLPQIKLRKEALKALCK------NYGFEGANPFSPAENQYKGEPAAEKPQI--------IYENDLKGIE  63
NDT L.1     6 IYFGAGWFTDRQNKAYKEAMEALKE------NPTIDLENSVPLDNQYKGIRVDEHPEYlhdkv-wataTYNNDLNGIK  77
gi 9279801  7 LYFGAGWFNEKQNKAYKEAMAALKE------NPTVDLENSVPLENQYKGIRIDEHPQYlhnie-wasaTYHNDLVGIK  78
gi 14195395 7 IYLAGPLFTLAEINDRKQQASLIRKtfkdelpNYELD---LFNPIEVNDELGANAHKPNIf------FYESDIKFID   74
gi 12723374 11 VYLAAPFFSESQIKKVELLENALSK------NKTVANFFSPMRCQHPESLPQEVEAFtpew--akaTMENDVNEVN   78
gi 14026127 278 IYLAAPFFDLGQRWLVEESRRALLQ-----AGAQVFSPIHEVGPGAAEV----------------VAPADLAGIE  331
gi 2688347  8 IYLASPFFKEEIKLRDEVIKFLEE------FNLE---VFSPEHHAVKKMGLLEKVDYkfanrdirekIREVDLKELv  76
gi 4678672  20 VYLAGDLVFRPNAIELFDELKEICK------DAGVQSVAPFDGQEGVEEMAPGAETSLK--------IAELDRKLMD  82
gi 9945974  42 LYLAGPDVFRADAVAHGEALKALCA------RYGFEGLYPLDNALPKQLAEPREQAAW--------IYRANIGLIE  103
gi 9945975  4 IYLAGPDVFRPDAEAHGETLKALCA------EFGFVGLYPLDHALPADIREPAAQAAW--------IYRANVGLIE  65
gi 13423604 7 LWLAGPEAWLPDLDLIQTSRQRALCL----ESGFE---ALAPARMPISDTGDELEARQ--------FYATRMAQLR  66
RCL        12 VFFCGSIRGGRED-------QALYArivsrlrRYGKVLTEHVADALEPLGEEAACGDQF-------IHEQDLNWLQ  74

90       100       110       120       130       140       150       160
              ....|....*....|....*....|....*....|....*....|....*....|....*....|....*....|
consensus  64 QADIVLANVDPF----EEDSGTAFELGYALALGKPVYAFFKDKreyaeTy-----------------------rd 111
NDT L.1    78 TNDIMLGVYIPD----EEBVGLGMELGYALLSQGKYVLLVIPDE---------------------------    116
gi 9279801 79 TSDVLLGVYLPQ----EEHVGLGMELGYPLSQGKLFFWFSHMK----------------------------    117
gi 14195395 75 QTDIAIIDIDNT------DDGTMAEMGYPVALQKHVKPTLKIYilntdwr---------------------    120
gi 12723374 79 KADIIVAIVDFDh-qDTDSSTAWELGYAIALEKPTYLIRFED---------------------------vh 119
gi 14026127 332 DCDVLLAIVNGM------DPGTVFEAGYAIRKGIPVVALAENSre-------------------------    370
gi 2688347 77 SSDIVLALVNVV------DSSTAYERGFAFAKKIPSIDPFKDKqdsdfynlmysdcaaafsnykdlregiltEkelwikf 150
gi 4678672 83 RCDGGIFCLDPFrrapDMDPGTAVELGYMAAQGKPLAGFTTDGrmypekvrsyrkqawgdalk-prftkggsgmedad 160
gi 9945974 104 RADAVLANLNFFrg-aEPDSGTAFEVGYATALGKPVGYGVDDAgsyaerirrhapeli----------gedptrdrd 169
gi 9945975 66 RADCVLANLEPFrg-sEPDSGTAFEVGYALAIGKPVYAYLSDAgayaerlarlapewl------------gehpgedrd 131
gi 13423604 67 QADAGVINLTPFrg-pAADTATVFEAGVLAGLGKPTFAYMNVTselraeyvarvdadlga----------idenrvwrdpd 137
RCL        75 QADVVVAEVTQP-----SLGVGYELGRAVALGKPILCLFRPQ--------------------------- 111

170       180
              ....|....*....|....*....|...
consensus 112 gcmneDFGKPLnLMLIAGLSDNAR    134
NDT L.1   117 -----DYGKPINLMSWGVSDNVI     134
gi 9279801 118 -----DYGKPIILMSWGVCDNAS    135
gi 14195395 121 khrneVLNKFLDGMILSHCQYFT   143
gi 12723374 120 ------TIPANIM---LTERNR    132
gi 14026127 371 -----eDLKMFVGSGATVTSDFAT  389
gi 2688347 151 kgdneNFRTFFDYLKAKLGNKLjK  173
gi 4678672 161 glivhSEGFLQNVMTEGFIRMSG   183
gi 9945974 170 gmtleEFGLPLNLMLAVPATLVV   192
gi 9945975 132 gwqleGFGLPLNLMLAVPSRLVA   154
gi 13423604 138 gcmieDHGLPETVM---LWGEAR   157
RCL       112 ------SGRVLSAMIRGAADGSR   128
```

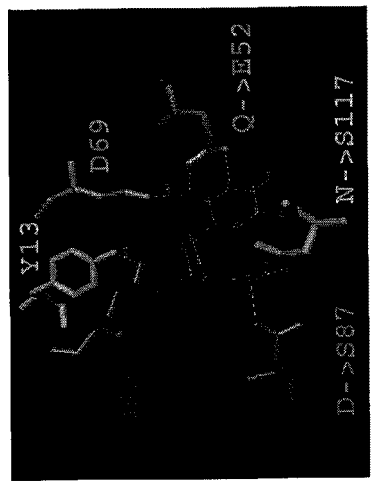

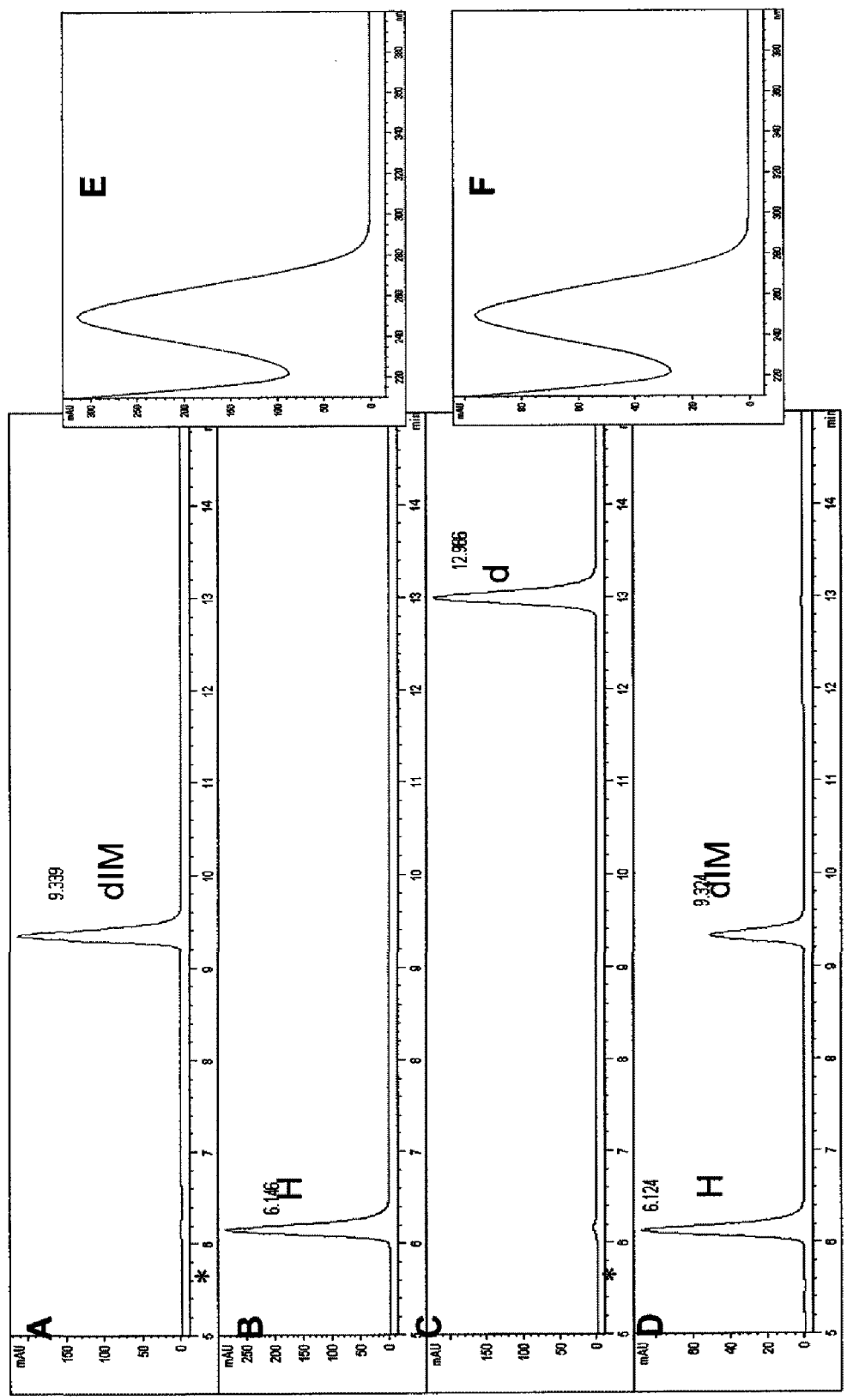

FIG 8

CLUSTAL X (1.83.1) multiple sequence alignment

```
              1         10        20        30        40        50        60
Rc1mouse      MAASGELVPC-------------SVYFCGSIRGGREDQALYSRIVSRLRRYGKVLTEHVA        SEQ ID No.: 10      NM_207161
Rc1rat        MAASGEQAPC-------------SVYFCGSIRGGREDQALYARIVSRLRRYGKVLTEHVA        SEQ ID No.: 8       AAB95314
Rc1human      MAAAMVPGRS--ESWERGEPGRPALYFCGSIRGGREDRTLYERIVSRLRRFGTVLTEHVA        SEQ ID No.: 6       AAB96766
Rc1canis      MAAAAAGARERREPGQPGQPGRRALYFCGSVRGGREDRALYGRIVSRLRRFGAVITEHVA        SEQ ID No.: 24      XM_538931
Equus         MAATMAAARE------RGEPGRRALYFCGSIRGGRDDRALYKRIVSRLRRFGTVLTEYVA        SEQ ID No.: 26      XM_001497421
Rc1Bos        MAAAAAAGTV--------DPGRLSLYFCGSIRGGREDRELYVRIVSRLRRFGVVITEHVA        SEQ ID No.: 28      XP_869908
Danio         ------------------MNIYFCGSIRGGRQDVVIYQTIVKKLQQYGNVLTEHVS            SEQ ID No.: 30      XM_685209
                                   :*****:*****:*  :* **.:*::*  ****:*:

61        70        80        90       100       110       120
Rc1mouse      DAELEPRGEEAAGGDQFIHERDLAWLRQADVVVAEVTQPSLGVGYELGRAVALGKPILCL        SEQ ID No.: 10
Rc1rat        DAELEPLGEEAAGGDQFIHEQDLNWLQQADVVVAEVTQPSLGVGYELGRAVALGKPILCL        SEQ ID No.: 8
Rc1human      AAELGARGEEAAGGDRLIHEQDLEWLQQADVVVAEVTQPSLGVGYELGRAVAFNKRILCL        SEQ ID No.: 6
Rc1dog        AAELGARGEEAAGGDRFIYERDLAWLQQADVVVAEVTQPSLGVGYELGQAMALNKRILCL        SEQ ID No.: 24
Equus         APDLG---EEAAGGDKLIHERDLAWLQQADVVVAEVTQPSLGVGYELGRAVALNKRILCL        SEQ ID No.: 26
Rc1bovin      AAEVDESGEEAAGGDKLIHDRDLAWLQQADVVVAEVTQPSLGVGYELGRAVALHKPVLCL        SEQ ID No.: 28
Danio         YDSLSDKGEDKDG-DKAIHDRDVQWLTMSDVIVAEVTQPSLGVGYELGRAVAMNKRILCL        SEQ ID No.: 30
              .:   * **: *::::  **  .:**:*************.*:.:*  :* ****

121       130       140       150       160       170       180
Rc1mouse      FRPQSGRVLSAMIRGAADGSRFQVWDYAEEEVETMLHRYFEAYLPQGTASSSNPSACLNP        SEQ ID No.: 10
Rc1rat        FRPQSGRVLSAMIRGAADGSRFQVWDYAEGEVETMLHRYFEAYLPQKTASSSHPSA----        SEQ ID No.: 8
Rc1human      FRPQSGRVLSAMIRGAADGSRFQVWDYEEGEVEALLDRYFEADPPGQVAASPDPTT----        SEQ ID No.: 6
Rc1dog        FRPQSGRVLSAMIRGAADGSRFQVLDYEEGQVEAMLDQYFEADP----------------        SEQ ID No.: 24
Equus         FRPQSGRVLSAMIRGAADGLRFQVWDYEEGEVEAMLDRYFEADPSEEVAASPEPTA----        SEQ ID No.: 26
Rc1bovin      FRPKSGRVLSAMIRGAANGSRFQVPGVG-------LRGSRSGGPARSVLRC---------        SEQ ID No.: 28
Danio         FRPFSGKVLSAMIRGASAKPLFQVQDYKEDEVENILEEYFETLTKN--------------        SEQ ID No.: 30
              *** **.:******** *          *

181
Rc1mouse      TVLEKI    SEQ ID No.: 10
Rc1rat        ------    SEQ ID No.: 8
Rc1human      ------    SEQ ID No.: 6
Rc1dog        ------    SEQ ID No.: 24
Equus         ------    SEQ ID No.: 26
Rc1bovin      ------    SEQ ID No.: 28
Danio         ------    SEQ ID No.: 30
```

```
                         SEQUENCE LISTING

<160> NUMBER OF SEQ ID NOS: 30

<210> SEQ ID NO 1
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 1
cgcgaaatta atacgactca ctatagggg                                        29

<210> SEQ ID NO 2
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 2
gcccggccca gcgcatagcc aacacccaag                                       30

<210> SEQ ID NO 3
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 3
ggggttatgc tagttattgc tcagcgg                                          27

<210> SEQ ID NO 4
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 4
cttgggtgtt ggctatgcgc tgggccgggc                                       30

<210> SEQ ID NO 5
<211> LENGTH: 525
<212> TYPE: DNA
<213> ORGANISM: Homo sapiens
```

<400> SEQUENCE: 5

```
atggctgctg ccatggtgcc ggggcgcagc gagagctggg agcgcgggga gcctggccgc    60
ccggccctgt acttctgcgg gagcattcgc ggcggacgcg aggacaggac gctgtacgag   120
cggatcgtgt ctcggctgcg gcgattcggg acagtgctca ccgagcacgt ggcggccgcc   180
gagctgggcg cgcgcgggga agaggctgct gggggtgaca ggctcatcca tgagcaggac   240
ctggagtggc tgcagcaggc ggacgtggtc gtggcagaag tgacacagcc atccttgggt   300
gtaggctatg agctgggccg ggccgtggcc tttaacaagc ggatcctgtg cctgttccgc   360
ccgcagtctg gccgcgtgct ttcggccatg atccggggag cagcagatgg ctctcggttc   420
caggtgtggg actatgagga gggagaggtg gaggccctgc tggatcgata cttcgaggct   480
gatcctccag ggcaggtggc tgcctcccct gacccaacca cttga                  525
```

<210> SEQ ID NO 6
<211> LENGTH: 174
<212> TYPE: PRT
<213> ORGANISM: Homo sapiens

<400> SEQUENCE: 6

```
Met Ala Ala Ala Met Val Pro Gly Arg Ser Glu Ser Trp Glu Arg Gly
1               5                   10                  15

Glu Pro Gly Arg Pro Ala Leu Tyr Phe Cys Gly Ser Ile Arg Gly Gly
            20                  25                  30

Arg Glu Asp Arg Thr Leu Tyr Glu Arg Ile Val Ser Arg Leu Arg Arg
        35                  40                  45

Phe Gly Thr Val Leu Thr Glu His Val Ala Ala Glu Leu Gly Ala
    50                  55                  60

Arg Gly Glu Glu Ala Ala Gly Gly Asp Arg Leu Ile His Glu Gln Asp
65                  70                  75                  80

Leu Glu Trp Leu Gln Gln Ala Asp Val Val Ala Glu Val Thr Gln
                85                  90                  95

Pro Ser Leu Gly Val Gly Tyr Glu Leu Gly Arg Ala Val Ala Phe Asn
            100                 105                 110

Lys Arg Ile Leu Cys Leu Phe Arg Pro Gln Ser Gly Arg Val Leu Ser
        115                 120                 125

Ala Met Ile Arg Gly Ala Ala Asp Gly Ser Arg Phe Gln Val Trp Asp
    130                 135                 140

Tyr Glu Glu Gly Glu Val Glu Ala Leu Leu Asp Arg Tyr Phe Glu Ala
145                 150                 155                 160

Asp Pro Pro Gly Gln Val Ala Ala Ser Pro Asp Pro Thr Thr
                165                 170
```

<210> SEQ ID NO 7
<211> LENGTH: 432
<212> TYPE: DNA
<213> ORGANISM: Rattus norvegicus

<400> SEQUENCE: 7

```
gggcgcgagg accaagcact gtatgcgcgg atcgtgtcgc ggctccgacg ctatgggaag    60
gtgctcactg agcacgtggc tgatgctgag ttggagccgc ttggggaaga ggctgctggg   120
ggtgaccagt tcatccatga gcaggacctg aactggctgc agcaagcaga tgtggtagtg   180
gcggaagtga cacagccatc cttgggtgtt ggctatgaac tgggccgggc agtagctctt   240
gggaagccaa ttctgtgcct gtttcgacca cagtctggcc gagtgctttc cgccatgatc   300
```

-continued

```
cgcggagcag cagatggctc gaggttccag gtatgggact acgcagaagg agaagtggag    360
accatgctcg atcggtactt tgaggcatat cttcctcaga agacggcttc ctccagtcac    420
ccaagtgcct ga                                                        432
```

<210> SEQ ID NO 8
<211> LENGTH: 163
<212> TYPE: PRT
<213> ORGANISM: Rattus norvegicus

<400> SEQUENCE: 8

```
Met Ala Ala Ser Gly Glu Gln Ala Pro Cys Ser Val Tyr Phe Cys Gly
1               5                   10                  15

Ser Ile Arg Gly Gly Arg Glu Asp Gln Ala Leu Tyr Ala Arg Ile Val
            20                  25                  30

Ser Arg Leu Arg Arg Tyr Gly Lys Val Leu Thr Glu His Val Ala Asp
        35                  40                  45

Ala Glu Leu Glu Pro Leu Gly Glu Glu Ala Ala Gly Gly Asp Gln Phe
    50                  55                  60

Ile His Glu Gln Asp Leu Asn Trp Leu Gln Gln Ala Asp Val Val Val
65                  70                  75                  80

Ala Glu Val Thr Gln Pro Ser Leu Gly Val Gly Tyr Glu Leu Gly Arg
                85                  90                  95

Ala Val Ala Leu Gly Lys Pro Ile Leu Cys Leu Phe Arg Pro Gln Ser
            100                 105                 110

Gly Arg Val Leu Ser Ala Met Ile Arg Gly Ala Ala Asp Gly Ser Arg
        115                 120                 125

Phe Gln Val Trp Asp Tyr Ala Glu Gly Glu Val Glu Thr Met Leu Asp
    130                 135                 140

Arg Tyr Phe Glu Ala Tyr Leu Pro Gln Lys Thr Ala Ser Ser Ser His
145                 150                 155                 160

Pro Ser Ala
```

<210> SEQ ID NO 9
<211> LENGTH: 522
<212> TYPE: DNA
<213> ORGANISM: Mus musculus

<400> SEQUENCE: 9

```
atggcggcat ccggggagct ggttccatgc tctgtgtact ctgcgggag catccgcggc     60 gggcgggaag accaagctct gtattcgcgg atcgtatccc ggctgcggcg ctatgggaag    120
gtgctcactg agcacgtggc tgatgctgag ttggagccgc gtgggaaga ggctgctggg    180 ggcgaccagt tcatccatga gcgggacctg gcctggctcc ggcaggccga tgtggtcgtg    240
gcagaagtga cacagccatc cctgggtgtt ggctacgaat gggccgggc agtagctctt    300 ggtaagccga tcctgtgcct gttccgacca cagtctggcc gagtgctttc cgccatgatc    360
cggggagcag ccgatggctc gaggttccag gtgtgggact acgcagagga agaagtggag    420
accatgctcc atcggtactt tgaggcttat cttcctcagg ggacggcttc ctccagtaac    480
ccaagtgcct gtcttaaccc tactgtatta gaaaaaattt aa                       522
```

<210> SEQ ID NO 10
<211> LENGTH: 173
<212> TYPE: PRT
<213> ORGANISM: Mus musculus -continued

<400> SEQUENCE: 10

```
Met Ala Ala Ser Gly Glu Leu Val Pro Cys Ser Val Tyr Phe Cys Gly
1               5                   10                  15

Ser Ile Arg Gly Gly Arg Glu Asp Gln Ala Leu Tyr Ser Arg Ile Val
            20                  25                  30

Ser Arg Leu Arg Arg Tyr Gly Lys Val Leu Thr Glu His Val Ala Asp
        35                  40                  45

Ala Glu Leu Glu Pro Arg Gly Glu Ala Ala Gly Asp Gln Phe
    50                  55                  60

Ile His Glu Arg Asp Leu Ala Trp Leu Arg Gln Ala Asp Val Val Val
65                  70                  75                  80

Ala Glu Val Thr Gln Pro Ser Leu Gly Val Gly Tyr Glu Leu Gly Arg
                85                  90                  95

Ala Val Ala Leu Gly Lys Pro Ile Leu Cys Leu Phe Arg Pro Gln Ser
            100                 105                 110

Gly Arg Val Leu Ser Ala Met Ile Arg Gly Ala Ala Asp Gly Ser Arg
        115                 120                 125

Phe Gln Val Trp Asp Tyr Ala Glu Glu Val Glu Thr Met Leu His
130                 135                 140

Arg Tyr Phe Glu Ala Tyr Leu Pro Gln Gly Thr Ala Ser Ser Ser Asn
145                 150                 155                 160

Pro Ser Ala Cys Leu Asn Pro Thr Val Leu Glu Lys Ile
                165                 170
```

<210> SEQ ID NO 11
<211> LENGTH: 134
<212> TYPE: PRT
<213> ORGANISM: Artificial Sequence
<220> FEATURE:
<223> OTHER INFORMATION: consensus sequence of aligned sequences

<400> SEQUENCE: 11

```
Ile Tyr Leu Ala Gly Pro Phe Phe Leu Pro Gln Ile Lys Leu Arg
1               5                   10                  15

Lys Glu Ala Leu Lys Ala Leu Cys Lys Asn Tyr Gly Phe Glu Gly Ala
            20                  25                  30

Asn Pro Phe Ser Pro Ala Glu Asn Gln Tyr Lys Gly Glu Pro Ala Ala
        35                  40                  45

Glu Lys Pro Gln Tyr Ile Tyr Glu Asn Asp Leu Lys Gly Ile Glu Gln
    50                  55                  60

Ala Asp Ile Val Leu Ala Asn Val Asp Pro Phe Glu Glu Asp Ser Gly
65                  70                  75                  80

Thr Ala Phe Glu Leu Gly Tyr Ala Leu Ala Leu Gly Lys Pro Val Tyr
                85                  90                  95

Ala Phe Phe Lys Asp Lys Arg Glu Tyr Ala Glu Arg Tyr Arg Asp Gly
            100                 105                 110

Cys Met Asn Glu Asp Phe Gly Lys Pro Leu Asn Leu Met Ile Ala Gly
        115                 120                 125

Leu Ser Asp Asn Ala Arg
    130
```

<210> SEQ ID NO 12
<211> LENGTH: 129
<212> TYPE: PRT
<213> ORGANISM: Lactobacillus leichmannii

<400> SEQUENCE: 12

Ile Tyr Phe Gly Ala Gly Trp Phe Thr Asp Arg Gln Asn Lys Ala Tyr
1               5                   10                  15

Lys Glu Ala Met Glu Ala Leu Lys Glu Asn Pro Thr Ile Asp Leu Glu
            20                  25                  30

Asn Ser Tyr Val Pro Leu Asp Asn Gln Tyr Lys Gly Ile Arg Val Asp
            35                  40                  45

Glu His Pro Glu Tyr Leu His Asp Lys Val Trp Ala Thr Ala Thr Tyr
        50                  55                  60

Asn Asn Asp Leu Asn Gly Ile Lys Thr Asn Asp Ile Met Leu Gly Val
65                  70                  75                  80

Tyr Ile Pro Asp Glu Glu Asp Val Gly Leu Gly Met Glu Leu Gly Tyr
                85                  90                  95

Ala Leu Ser Gln Gly Lys Tyr Val Leu Val Ile Pro Asp Glu Asp
            100                 105                 110

Tyr Gly Lys Pro Ile Asn Leu Met Ser Trp Gly Val Ser Asp Asn Val
            115                 120                 125

Ile

<210> SEQ ID NO 13
<211> LENGTH: 129
<212> TYPE: PRT
<213> ORGANISM: Lactobacillus helveticus

<400> SEQUENCE: 13

Leu Tyr Phe Gly Ala Gly Trp Phe Asn Glu Lys Gln Asn Lys Ala Tyr
1               5                   10                  15

Lys Glu Ala Met Ala Ala Leu Lys Glu Asn Pro Thr Val Asp Leu Glu
            20                  25                  30

Asn Ser Tyr Val Pro Leu Glu Asn Gln Tyr Lys Gly Ile Arg Ile Asp
            35                  40                  45

Glu His Pro Gln Tyr Leu His Asn Ile Glu Trp Ala Ser Ala Thr Tyr
        50                  55                  60

His Asn Asp Leu Val Gly Ile Lys Thr Ser Asp Val Leu Leu Gly Val
65                  70                  75                  80

Tyr Leu Pro Gln Glu Glu His Val Gly Leu Gly Met Glu Leu Gly Tyr
                85                  90                  95

Pro Leu Ser Gln Gly Lys Leu Phe Phe Trp Phe Ser His Met Lys Asp
            100                 105                 110

Tyr Gly Lys Pro Ile Ile Leu Met Ser Trp Gly Val Cys Asp Asn Ala
            115                 120                 125

Ser

<210> SEQ ID NO 14
<211> LENGTH: 137
<212> TYPE: PRT
<213> ORGANISM: Ureaplasma parvum

<400> SEQUENCE: 14

Ile Tyr Leu Ala Gly Pro Leu Phe Thr Leu Ala Glu Ile Asn Asp Arg
1               5                   10                  15

Lys Gln Gln Ala Ser Leu Ile Arg Lys Thr Phe Lys Asp Glu Leu Pro
            20                  25                  30

Asn Tyr Glu Leu Asp Leu Phe Asn Pro Ile Glu Val Asn Asp Glu Leu
            35                  40                  45

Gly Ala Asn Ala His Lys Pro Asn Ile Phe Phe Tyr Glu Ser Asp Ile

```
                 50                  55                  60
Lys Phe Ile Asp Gln Thr Asp Ile Ala Ile Asp Ile Asp Asn Thr
 65                  70                  75                  80

Asp Asp Gly Thr Met Ala Glu Met Gly Tyr Phe Val Ala Leu Gln Lys
                 85                  90                  95

His Val Lys Pro Thr Leu Lys Ile Tyr Ile Leu Asn Thr Asp Trp Arg
            100                 105                 110

Val His Lys His Arg Asn Glu Val Leu Asn Lys Phe Leu Asp Gly Met
            115                 120                 125

Ile Leu Ser His Cys Gln Tyr Phe Thr
            130                 135

<210> SEQ ID NO 15
<211> LENGTH: 122
<212> TYPE: PRT
<213> ORGANISM: Lactobacillus lactis

<400> SEQUENCE: 15

Val Tyr Leu Ala Ala Pro Phe Phe Ser Glu Ser Gln Ile Lys Lys Val
 1               5                  10                  15

Glu Leu Leu Glu Asn Ala Leu Ser Lys Asn Lys Thr Val Ala Asn Phe
                 20                  25                  30

Phe Ser Pro Met Arg Cys Gln His Pro Glu Ser Leu Pro Gln Glu Val
                 35                  40                  45

Glu Ala Phe Thr Pro Glu Trp Ala Lys Ala Thr Met Glu Asn Asp Val
                 50                  55                  60

Asn Glu Val Asn Lys Ala Asp Ile Ile Val Ala Ile Val Asp Phe Asp
 65                  70                  75                  80

His Gln Asp Thr Asp Ser Gly Thr Ala Trp Glu Leu Gly Tyr Ala Ile
                 85                  90                  95

Ala Leu Glu Lys Pro Thr Tyr Leu Ile Arg Phe Glu Asp Thr Ile Pro
            100                 105                 110

Ala Asn Ile Met Leu Thr Glu Arg Asn Arg
            115                 120

<210> SEQ ID NO 16
<211> LENGTH: 112
<212> TYPE: PRT
<213> ORGANISM: Mesorhizobium loti

<400> SEQUENCE: 16

Ile Tyr Leu Ala Ala Pro Phe Phe Asp Leu Gly Gln Arg Trp Leu Val
 1               5                  10                  15

Glu Glu Ser Arg Arg Ala Leu Leu Gln Ala Gly Ala Gln Val Phe Ser
                 20                  25                  30

Pro Ile His Glu Val Gly Pro Gly Ala Ala Glu Val Val Ala Pro Ala
                 35                  40                  45

Asp Leu Ala Gly Ile Glu Asp Cys Asp Val Leu Leu Ala Ile Val Asn
            50                  55                  60

Gly Met Asp Pro Gly Thr Val Phe Glu Ala Gly Tyr Ala Ile Arg Lys
 65                  70                  75                  80

Gly Ile Pro Val Val Ala Leu Ala Glu Asn Ser Arg Glu Glu Asp Leu
                 85                  90                  95

Lys Met Phe Val Gly Ser Gly Ala Thr Val Thr Ser Asp Phe Ala Thr
            100                 105                 110
```

```
<210> SEQ ID NO 17
<211> LENGTH: 166
<212> TYPE: PRT
<213> ORGANISM: Borrelia burgdorferi

<400> SEQUENCE: 17

Ile Tyr Leu Ala Ser Pro Phe Phe Lys Glu Glu Ile Lys Leu Arg
1               5                   10                  15

Asp Glu Val Leu Lys Phe Leu Glu Glu Phe Asn Leu Glu Val Phe Ser
            20                  25                  30

Pro Glu His His Ala Val Lys Lys Met Gly Leu Leu Glu Lys Val Asp
        35                  40                  45

Tyr Lys Phe Ala Asn Arg Asp Ile Arg Glu Lys Ile Arg Glu Val Asp
    50                  55                  60

Leu Lys Glu Leu Val Ser Ser Asp Ile Val Leu Ala Leu Val Asn Tyr
65                  70                  75                  80

Val Asp Ser Gly Thr Ala Tyr Glu Arg Gly Phe Ala Phe Ala Lys Lys
                85                  90                  95

Ile Pro Ser Ile Asp Phe Phe Lys Asp Lys Gln Asp Ser Asp Phe Tyr
            100                 105                 110

Asn Leu Met Tyr Ser Asp Cys Ala Ala Ala Phe Ser Asn Tyr Lys Asp
        115                 120                 125

Leu Arg Glu Gly Ile Leu Thr Phe Lys Glu Leu Trp Ile Lys Phe Lys
    130                 135                 140

Gly Asp Asn Glu Asn Phe Arg Thr Phe Phe Asp Tyr Leu Lys Ala Lys
145                 150                 155                 160

Leu Gly Asn Lys Leu Lys
                165

<210> SEQ ID NO 18
<211> LENGTH: 164
<212> TYPE: PRT
<213> ORGANISM: Schizosaccharomyces pombe

<400> SEQUENCE: 18

Val Tyr Leu Ala Gly Asp Leu Val Phe Arg Pro Asn Ala Ile Glu Leu
1               5                   10                  15

Phe Asp Glu Leu Lys Glu Ile Cys Lys Asp Ala Gly Val Gln Gly Val
            20                  25                  30

Ala Pro Phe Asp Gly Gln Glu Gly Val Glu Glu Met Ala Pro Gly Ala
        35                  40                  45

Glu Thr Ser Leu Lys Ile Ala Glu Leu Asp Arg Lys Leu Met Asp Arg
    50                  55                  60

Cys Asp Gly Gly Ile Phe Cys Leu Asp Pro Phe Arg Arg Ala Pro Asp
65                  70                  75                  80

Met Asp Pro Gly Thr Ala Val Glu Leu Gly Tyr Met Ala Ala Gln Gly
                85                  90                  95

Lys Pro Leu Ala Gly Phe Thr Thr Asp Gly Arg Met Tyr Pro Glu Lys
            100                 105                 110

Val Arg Ser Tyr Arg Lys Gln Ala Trp Gly Asp Ala Leu Lys Pro Arg
        115                 120                 125

Phe Thr Lys Gly Ser Gly Ser Met Glu Asp Ala Asp Gly Leu Ile
    130                 135                 140

Val His Ser Glu Gly Phe Leu Gln Asn Val Met Thr Glu Gly Phe Ile
145                 150                 155                 160

Arg Met Ser Gly
```

<210> SEQ ID NO 19
<211> LENGTH: 151
<212> TYPE: PRT
<213> ORGANISM: Pseudomonas aeruginosa

<400> SEQUENCE: 19

Leu Tyr Leu Ala Gly Pro Asp Val Phe Arg Ala Asp Ala Val Ala His
1               5                   10                  15

Gly Glu Ala Leu Lys Ala Leu Cys Ala Arg Tyr Gly Phe Glu Gly Leu
            20                  25                  30

Tyr Pro Leu Asp Asn Ala Leu Pro Lys Gln Leu Ala Glu Pro Arg Glu
        35                  40                  45

Gln Ala Ala Trp Ile Tyr Arg Ala Asn Ile Gly Leu Ile Glu Arg Ala
    50                  55                  60

Asp Ala Val Leu Ala Asn Leu Asn Phe Phe Arg Gly Ala Glu Pro Asp
65                  70                  75                  80

Ser Gly Thr Ala Phe Glu Val Gly Tyr Ala Thr Ala Leu Gly Lys Pro
                85                  90                  95

Val Tyr Gly Tyr Val Asp Asp Ala Gly Ser Tyr Ala Glu Arg Ile Arg
            100                 105                 110

Arg His Ala Pro Glu Leu Ile Gly Glu Asp Pro Thr Arg Asp Arg Asp
        115                 120                 125

Gly Met Thr Leu Glu Glu Phe Gly Leu Pro Leu Asn Leu Met Leu Ala
    130                 135                 140

Val Pro Ala Thr Leu Val Val
145                 150

<210> SEQ ID NO 20
<211> LENGTH: 151
<212> TYPE: PRT
<213> ORGANISM: Pseudomonas aeruginosa

<400> SEQUENCE: 20

Ile Tyr Leu Ala Gly Pro Asp Val Phe Arg Pro Asp Ala Glu Ala His
1               5                   10                  15

Gly Glu Thr Leu Lys Ala Leu Cys Ala Glu Phe Gly Phe Val Gly Leu
            20                  25                  30

Tyr Pro Leu Asp His Ala Leu Pro Ala Asp Ile Arg Glu Pro Ala Ala
        35                  40                  45

Gln Ala Ala Trp Ile Tyr Arg Ala Asn Val Gly Leu Ile Glu Arg Ala
    50                  55                  60

Asp Cys Val Leu Ala Asn Leu Glu Pro Phe Arg Gly Ser Glu Pro Asp
65                  70                  75                  80

Ser Gly Thr Ala Phe Glu Val Gly Tyr Ala Leu Ala Leu Gly Lys Pro
                85                  90                  95

Val Tyr Ala Tyr Leu Ser Asp Ala Gly Ala Tyr Ala Glu Arg Leu Ala
            100                 105                 110

Arg Leu Ala Pro Glu Trp Leu Gly Glu His Pro Gly Glu Asp Arg Asp
        115                 120                 125

Gly Trp Gln Leu Glu Gly Phe Gly Leu Pro Leu Asn Leu Met Leu Ala
    130                 135                 140

Val Pro Ser Arg Leu Val Ala
145                 150

<210> SEQ ID NO 21

```
<211> LENGTH: 151
<212> TYPE: PRT
<213> ORGANISM: Caulobacter crescentus

<400> SEQUENCE: 21

Leu Trp Leu Ala Gly Pro Glu Ala Trp Leu Pro Asp Leu Asp Leu Gln
1               5                   10                  15

Thr Ser Arg Gln Arg Ala Leu Cys Leu Glu Ser Gly Phe Glu Ala Leu
            20                  25                  30

Ala Pro Ala Arg Met Pro Ile Ser Asp Thr Gly Asp Glu Leu Glu Ala
        35                  40                  45

Arg Gln Phe Tyr Ala Thr Arg Met Ala Gln Leu Arg Gln Ala Asp Ala
    50                  55                  60

Gly Val Ile Asn Leu Thr Pro Phe Arg Gly Pro Ala Ala Asp Thr Ala
65                  70                  75                  80

Thr Val Phe Glu Ala Gly Val Leu Ala Gly Leu Gly Lys Pro Thr Phe
                85                  90                  95

Ala Tyr Met Asn Val Thr Ser Glu Leu Arg Ala Glu Tyr Val Ala Arg
            100                 105                 110

Val Asp Ala Asp Leu Gly Ala Ile Leu Asp Glu Asn Arg Val Trp Arg
        115                 120                 125

Asp Pro Asp Gly Cys Met Ile Glu Asp His Gly Leu Pro Glu Thr Val
    130                 135                 140

Met Leu Trp Gly Glu Ala Arg
145                 150

<210> SEQ ID NO 22
<211> LENGTH: 117
<212> TYPE: PRT
<213> ORGANISM: Homo sapiens

<400> SEQUENCE: 22

Val Tyr Phe Cys Gly Ser Ile Arg Gly Gly Arg Glu Asp Gln Ala Leu
1               5                   10                  15

Tyr Ala Arg Ile Val Ser Arg Leu Arg Arg Tyr Gly Lys Val Leu Thr
            20                  25                  30

Glu His Val Ala Asp Ala Glu Leu Glu Pro Leu Gly Glu Glu Ala Ala
        35                  40                  45

Gly Gly Asp Gln Phe Ile His Glu Gln Asp Leu Asn Trp Leu Gln Gln
    50                  55                  60

Ala Asp Val Val Val Ala Glu Val Thr Gln Pro Ser Leu Gly Val Gly
65                  70                  75                  80

Tyr Glu Leu Gly Arg Ala Val Ala Leu Gly Lys Pro Ile Leu Cys Leu
                85                  90                  95

Phe Arg Pro Gln Ser Gly Arg Val Leu Ser Ala Met Ile Arg Gly Ala
            100                 105                 110

Ala Asp Gly Ser Arg
        115

<210> SEQ ID NO 23
<211> LENGTH: 600
<212> TYPE: DNA
<213> ORGANISM: Canis familiaris

<400> SEQUENCE: 23
cggcggcggg gatgtcgggg atggcggcgg cggcggccgg agcgcgggag cgcagggagc      60
cgggccagcc gggccagccg ggccgccgag cgctgtactt ctgcgggagc gtccgcggcg     120
```

```
gccgcgagga ccgggcgctg tacgggagga tcgtgtcgcg gctgcggcgc ttcggggcgg    180
tgctcacgga gcacgtggcg gccgccgagc tgggcgcgcg cggggaagag gctgctgggg    240
gcgacaggtt catctacgag cgggacctgg cttggctgca gcaggcagat gtggtggtgg    300
cagaagtgac ccagccatcg ttgggcgtgg gctatgagct gggccaggcc atggccctca    360
ataagcggat cttgtgcctc ttccgtccgc agtctggccg agtgctttca gccatgatcc    420
ggggagcggc agacggctca aggttccagg tgttggacta tgaagagggc caggtggagg    480
ccatgctgga tcaatacttt gaggctgacc ctccctagca ggtggctgcc tcccctgacc    540
caactgcttg ccttagcccc actttgttaa ttcttctaat cccagactct tagtacccTT    600
```

<210> SEQ ID NO 24
<211> LENGTH: 164
<212> TYPE: PRT
<213> ORGANISM: Canis familiaris

<400> SEQUENCE: 24

Met Ala Ala Ala Ala Gly Ala Arg Glu Arg Arg Glu Pro Gly Gln
1               5                   10                  15

Pro Gly Gln Pro Gly Arg Arg Ala Leu Tyr Phe Cys Gly Ser Val Arg
                20                  25                  30

Gly Gly Arg Glu Asp Arg Ala Leu Tyr Gly Arg Ile Val Ser Arg Leu
            35                  40                  45

Arg Arg Phe Gly Ala Val Leu Thr Glu His Val Ala Ala Ala Glu Leu
50                  55                  60

Gly Ala Arg Gly Glu Glu Ala Ala Gly Gly Asp Arg Phe Ile Tyr Glu
65                  70                  75                  80

Arg Asp Leu Ala Trp Leu Gln Gln Ala Asp Val Val Val Ala Glu Val
                85                  90                  95

Thr Gln Pro Ser Leu Gly Val Gly Tyr Glu Leu Gly Gln Ala Met Ala
                100                 105                 110

Leu Asn Lys Arg Ile Leu Cys Leu Phe Arg Pro Gln Ser Gly Arg Val
            115                 120                 125

Leu Ser Ala Met Ile Arg Gly Ala Ala Asp Gly Ser Arg Phe Gln Val
130                 135                 140

Leu Asp Tyr Glu Glu Gly Gln Val Glu Ala Met Leu Asp Gln Tyr Phe
145                 150                 155                 160

Glu Ala Asp Pro

<210> SEQ ID NO 25
<211> LENGTH: 444
<212> TYPE: DNA
<213> ORGANISM: Equus caballus

<400> SEQUENCE: 25

```
ttctgcggga gcatccgcgg cggacgcgac gaccgggcgc tgtacaagcg gatcgtgtcg    60
cggctgcggc gcttcgggac cgtgctcacc gagtacgtgg cggctcccga cctgggggaa   120
gaggctgctg ggggtgacaa gctcatccat gagcgagacc tggcctggct gcagcaggct   180
gatgtggtcg tggcagaagt gacccagcca tccttgggtg taggctacga gctgggccgg   240
gccgtagccc tcaataagcg aatcctgtgc ctcttccgcc gcagtctgg ccgagtgctt    300 tcagccatga tccgcggagc agcagatggc ttgcggttcc aggtatggga ctatgaagag   360
ggagaggtgg aggccatgct ggatcgatac tttgaggctg atccttctga ggaggtggct   420
``` gcctccctg agccaaccgc ttga                                                444

<210> SEQ ID NO 26
<211> LENGTH: 167
<212> TYPE: PRT
<213> ORGANISM: Equus caballus

<400> SEQUENCE: 26

Met Ala Ala Thr Met Ala Ala Ala Arg Glu Arg Gly Glu Pro Gly Arg
1               5                   10                  15

Arg Ala Leu Tyr Phe Cys Gly Ser Ile Arg Gly Gly Arg Asp Asp Arg
            20                  25                  30

Ala Leu Tyr Lys Arg Ile Val Ser Arg Leu Arg Arg Phe Gly Thr Val
        35                  40                  45

Leu Thr Glu Tyr Val Ala Ala Pro Asp Leu Gly Glu Ala Ala Gly
    50                  55                  60

Gly Asp Lys Leu Ile His Glu Arg Asp Leu Ala Trp Leu Gln Gln Ala
65                  70                  75                  80

Asp Val Val Ala Glu Val Thr Gln Pro Ser Leu Gly Val Gly Tyr
                85                  90                  95

Glu Leu Gly Arg Ala Val Ala Leu Asn Lys Arg Ile Leu Cys Leu Phe
            100                 105                 110

Arg Pro Gln Ser Gly Arg Val Leu Ser Ala Met Ile Arg Gly Ala Ala
        115                 120                 125

Asp Gly Leu Arg Phe Gln Val Trp Asp Tyr Glu Glu Gly Glu Val Glu
    130                 135                 140

Ala Met Leu Asp Arg Tyr Phe Glu Ala Asp Pro Ser Glu Glu Val Ala
145                 150                 155                 160

Ala Ser Pro Glu Pro Thr Ala
                165

<210> SEQ ID NO 27
<211> LENGTH: 571
<212> TYPE: DNA
<213> ORGANISM: Bos Taurus

<400> SEQUENCE: 27
ccggcggggc ctgcggggcc cgggatggcg gcggcggcgg cggctggaac cgtggatccg        60
ggtcgtctct ccctgtactt ctgcgggagt atccgtggcg gacgcgagga tcgggaactg       120
tacgtgcgca tcgtgtctcg cctccggcgc ttcggggtgg tgcttaccga gcatgtggcg       180
gccgccgagg tggacgagag cggggaagag gctgctggag gcgacaagct catccatgat       240
cgggacctgg cctggctgca gcaggcagat gtggtcgtgg cagaagtgac ccagcccctct      300
ctggggggtag ctatgagct gggccgggcc gtagccctcc acaaaccagt cctgtgcctg       360
tttcgcccaa agtctggccg agtgctctca gccatgatcc ggggagcagc caatggctcc       420
aggttccagg ttcaggtgt gggactacga ggaagcagaa gtggaggccc tgctagatcg       480
gtactttgag gcgtatcctc ctgagcaggt ggctgcctct cctgacccaa cagcttgact       540
tcaccccagt ttttattaaa ttctcctgat c                                      571

<210> SEQ ID NO 28
<211> LENGTH: 154
<212> TYPE: PRT
<213> ORGANISM: Bos Taurus

<400> SEQUENCE: 28

```
Met Ala Ala Ala Ala Ala Gly Thr Val Asp Pro Gly Arg Leu Ser
1               5                  10                  15

Leu Tyr Phe Cys Gly Ser Ile Arg Gly Arg Glu Asp Arg Glu Leu
            20                  25                  30

Tyr Val Arg Ile Val Ser Arg Leu Arg Arg Phe Gly Val Val Leu Thr
        35                  40                  45

Glu His Val Ala Ala Glu Val Asp Glu Ser Gly Glu Glu Ala Ala
    50                  55                  60

Gly Gly Asp Lys Leu Ile His Asp Arg Asp Leu Ala Trp Leu Gln Gln
65                  70                  75                  80

Ala Asp Val Val Ala Glu Val Thr Gln Pro Ser Leu Gly Val Gly
                85                  90                  95

Tyr Glu Leu Gly Arg Ala Val Ala Leu His Lys Pro Val Leu Cys Leu
            100                 105                 110

Phe Arg Pro Lys Ser Gly Arg Val Leu Ser Ala Met Ile Arg Gly Ala
        115                 120                 125

Ala Asn Gly Ser Arg Phe Gln Val Pro Gly Val Gly Leu Arg Gly Ser
    130                 135                 140

Arg Ser Gly Gly Pro Ala Arg Ser Val Leu
145                 150
```

<210> SEQ ID NO 29
<211> LENGTH: 666
<212> TYPE: DNA
<213> ORGANISM: Danio rerio

<400> SEQUENCE: 29

```
gcagtttatc tgaacttccc gtgaatgctg tgctgctgag aaaagcacgc ttgtatcaca    60
gaagaaagac gaggactcct gcaaattatg aacatatact tttgcggaag cattcgggga   120
gggcgacagg acgtggttat ttatcagaca atagtgaaga agttgcagca gtatggcaat   180
gttttaaccg agcatgtgag ttatgacagc ctgtctgaca agggtgaaga taaagatgga   240
gataaagcca ttcatgatcg ggatgtgcag tggctgacga tgtctgacgt gatagtagca   300
gaagtgacgc agccatcttt aggtgttggt tatgaactgg gccgagctgt ggcaatgaac   360
aagaggatcc tctgtctctt cagacctttt tctggaaaag tgctctccgc catgatcaga   420
ggagcgtcag ccaaaccact cttccaagta caagactaca agaggacga agtggagaac   480
atcttggagg aatattttga gactctcact aagaactgat gagcagctga tcataacaaa   540
tcctatgtgc tgctcttatt caaatcaaca ggactgcttt ggtaagcatt tgtagtgaaa   600
atgcatatta agcatacaca gtgtattgtt acttgctctt gaataaatct ggttttgtta   660
acaaca                                                              666
```

<210> SEQ ID NO 30
<211> LENGTH: 143
<212> TYPE: PRT
<213> ORGANISM: Danio rerio

<400> SEQUENCE: 30

```
Met Asn Ile Tyr Phe Cys Gly Ser Ile Arg Gly Gly Arg Gln Asp Val
1               5                  10                  15

Val Ile Tyr Gln Thr Ile Val Lys Lys Leu Gln Gln Tyr Gly Asn Val
            20                  25                  30

Leu Thr Glu His Val Ser Tyr Asp Ser Leu Ser Asp Lys Gly Glu Asp
        35                  40                  45
```

-continued

```
Lys Asp Gly Asp Lys Ala Ile His Asp Arg Asp Val Gln Trp Leu Thr
    50                  55                  60

Met Ser Asp Val Ile Val Ala Glu Val Thr Gln Pro Ser Leu Gly Val
65                  70                  75                  80

Gly Tyr Glu Leu Gly Arg Ala Val Ala Met Asn Lys Arg Ile Leu Cys
                85                  90                  95

Leu Phe Arg Pro Phe Ser Gly Lys Val Leu Ser Ala Met Ile Arg Gly
            100                 105                 110

Ala Ser Ala Lys Pro Leu Phe Gln Val Gln Asp Tyr Lys Glu Asp Glu
        115                 120                 125

Val Glu Asn Ile Leu Glu Glu Tyr Phe Glu Thr Leu Thr Lys Asn
    130                 135                 140
```

US 7,781,394 B2

METHODS FOR IDENTIFYING ANTI-TUMOR AND/OR ANTI-ANGIOGENESIS DRUGS WITH DEOXYNUCLEOSIDE 5'-MONOPHOSPHATE N-GLYCOSIDASE AS THE TARGET

CROSS-REFERENCE TO RELATED APPLICATIONS

The present application claims the benefit of U.S. provisional application Ser. No. 60/865,483 filed Nov. 13, 2006.

BACKGROUND OF THE INVENTION

1. Field of the Invention

The present invention relates to a novel target for identifying and/or screening antitumor and/or antiangiogenesis agents using the rcl encoded deoxynucleoside 5'monophosphate N-glycosidase.

2. Description of the Related Art

The c-Myc transcription factor plays an important role in the regulation of the cell cycle, cellular transformation and apoptosis (Eisenman, R. N. (2001) *Genes Dev* 15, 2023-30) as well as in the genesis of many human cancers (Nesbit, et al (1999) *Oncogene* 18, 3004-16). The deregulation of MYC expression by chromosomal translocation, amplification or altered signal transduction is commonly found in human cancers (Escot, et al (1986) *Proc Natl Acad Sci USA* 83, 4834-8; Little, et al (1983) *Nature* 306, 194-6.). In order to elucidate the mechanisms by which c-Myc contributes to tumorigenesis, several approaches have been used to identify its target genes that are compiled in a database (http://www.myccancergene.org/site/mycTargetDB.asp).

Rcl was identified as a c-Myc target by representational difference analysis between non-adherent Rat1a fibroblasts and Rat 1a cells transformed by MYC (Lewis, et al (1997) *Mol Cell Biol* 17, 4967-78). Rcl is expressed at a low level in untransformed cell lines while it is significantly elevated in breast cancer and lymphoma cell lines (Lewis, et al (1997) *Mol Cell Biol* 17, 4967-78). Moreover, Rcl is one of the most responsive target to Myc activation in vitro and in Myc-induced transgenic lymphoma (Kim, et al (2003) *Mol Cell* 11, 1177-88; Keller, et al (2005) *Oncogene* 24, 6231-40), and Rcl has been shown to be a direct Myc target in a human lymphoma cell model (Zeller, et al. (2003) *Genome Biol* 4, R69). Serial analysis of gene expression studies revealed that Rcl is also highly expressed in human glioblastoma multiforme as compared with normal human brain (information from the UniGene database, at NCBI). Furthermore, Rcl is among the top 50 genes whose overexpression distinguishes between benign and malignant prostate tissues (Rhodes, et al (2002) *Cancer Res* 62, 4427-33). Functionally, Rcl has transforming activity in Rat1a cells when coexpressed with either vascular endothelial growth factor (VEGF) or lactate dehydrogenase (LDHA) (Lewis, et al (2000) *Cancer Res* 60, 6178-83). Altogether these data suggest that RCL could be a prime therapeutic target.

RCL appears to be a nuclear 22 kDa protein with yet unknown function. The closest relative of RCL protein is the nucleoside 2-deoxyribosyltransferase family (EC: 2.4.2.6). (pfam 05014) that catalyzes the reversible transfer of the deoxyribosyl moiety from a deoxynucleoside donor to an acceptor nucleobase (Macnutt, W. S. (1952) *Biochem J* 50, 384-97; Uerkvitz, W. (1971) *Eur J Biochem* 23, 387-95; Holguin-Hueso, J. & Cardinaud, R. (1972) *FEBS Lett* 20, 171-173). Here, we report the purification and characterization of the recombinant RCL from rat. RCL is a deoxynucleoside 5'-monophosphate N-glycosidase, a function never described before.

SUMMARY OF THE INVENTION

On the basis of discovering the activity of the RCL protein, the present invention provides, in one embodiment, a method for identifying a substance with antitumor activity by contacting at least one sample comprising an rcl deoxynucleoside 5'-monophosphate N-glycosidase or a cell expressing deoxynucleoside 5'-monophosphate N-glycosidase with the substance; measuring the deoxynucleoside 5'-monophosphate N-glycosidase in the sample; comparing the deoxynucleoside 5'-monophosphate N-glycosidase in the sample with at least one control sample comprising an rcl deoxynucleoside 5'-monophosphate N-glycosidase or a cell expressing deoxynucleoside 5'-monophosphate N-glycosidase with the substance, selecting the substance which reduces in at least one sample deoxynucleoside 5'-monophosphate N-glycosidase activity compared to a control sample which had not be contacted with the substance; administering the selected substance to an animal comprising a tumor; evaluating at least one of indicia selected from the group consisting of size of the tumor, growth of the tumor, rate of growth of the tumor, and regression of the tumor; and comparing the at least one indicia to an animal also comprising a tumor but to which the selected substance was not administered, wherein a decrease in size and/or decrease in the rate of tumor growth is indicative that the substance has antitumor activity.

Another embodiment of the present invention is a method for identifying a substance with angiogenesis inhibitory activity, by testing for an inhibitor of rcl deoxynucleoside 5'-monophosphate N-glycosidase activity as above and then testing the selected substance for angiogenesis inhibitory activity.

Another embodiment of the present invention is a method of using a rcl deoxynucleoside 5'-monophosphate N-glycosidase as research tool for identifying a substance with antitumor activity. In this method, the rcl deoxynucleoside 5'-monophosphate N-glycosidase can comprise at least one amino acid sequence selected from the group consisting of SEQ ID NO:6, SEQ ID NO:8, an amino acid sequence that is 90% identical to SEQ ID NO:6 and which has deoxynucleoside 5'-monophosphate N-glycosidase activity; an amino acid sequence that is 90% identical to SEQ ID NO:8 and which has deoxynucleoside 5'-monophosphate N-glycosidase activity, an amino acid sequence that is 95% identical to SEQ ID NO:6 and which has deoxynucleoside 5'-monophosphate N-glycosidase activity, and an amino acid sequence that is 95% identical to SEQ ID NO:8 and which has deoxynucleoside 5'-monophosphate N-glycosidase activity.

Another embodiment of the present invention is a method of using a rcl deoxynucleoside 5'-monophosphate N-glycosidase as research tool for identifying a substance with angiogenesis inhibitory activity. In this method, the rcl deoxynucleoside 5'-monophosphate N-glycosidase can comprise at least one amino acid sequence selected from the group consisting of SEQ ID NO:6, SEQ ID NO:8, an amino acid sequence that is 90% identical to SEQ ID NO:6 and which has deoxynucleoside 5'-monophosphate N-glycosidase activity; an amino acid sequence that is 90% identical to SEQ ID NO:8 and which has deoxynucleoside 5'-monophosphate N-glycosidase activity, an amino acid sequence that is 95% identical to SEQ ID NO:6 and which has deoxynucleoside 5'-monophosphate N-glycosidase activity, and an amino acid sequence that is 95% identical to SEQ ID NO:8 and which has deoxynucleoside 5'-monophosphate N-glycosidase activity

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1. SDS-PAGE analysis of purified native and N-terminal His tagged RCL. Panel A) Native RCL. Lane 1: 10 μg of total protein from post-centrifugation lysates of BL21 (DE3)pLysS pET24dRcl cell. Lane 2: 10 μg of protein after ion exchange on a Q-fast flow column. Lane 3: 10 μg of proteins after gel filtration on Sephacryl S-200 column. Panel B) His tagged RCL. Lane 1: 0 μg of total protein from post-centrifugation lysates of BL21 (DE3)pLysS pET8aRcl. Lane 2: 10 μg of protein after TALON column. Lane 3: 10 μg of proteins after gel filtration on Sephacryl S-200. Samples were separated on a 12% SDS-PAGE stained with Coomassie Blue. Molecular weight markers (kDa) on the left side of each gel (Pre-stained SDS-PAGE standards low range from Bio-Rad) are shown: phosphorylase B (116 kDa), bovine serum albumin (80 kDa), ovalbumin (52.5 kDa), carbonic anhydrase (34.9 kDa), soybean trypsin inhibitor (29.9 kDa), and lysozyme (21.8 kDa).

FIG. 3. Alignment of the nucleoside 2-deoxyribosyltransferase cluster of orthologs (COG3613) (SEQ ID NOS:11-22). Amino acids that participate in the catalytic active site of *Lactobacillus leichmannii* are indicated in bold characters. gi 9279801: NTD *Lactobacillus helveticusi*, gi 14195395: Q9PR82 *Ureaplasma parvum*, gi 12723374: yejD *Lactococcus lactis*, gi 14026127: m 116424 *Mesorhizobium loti*, gi 2688347: AAC 68812 *Borrelia burgdorferi*, gi 4678672: CAB 41051 *Schizosaccharomyces pombe*, gi 9945974: AAG 03534 *Pseudomonas aeruginosa* PAO1, gi 9945975: AAG 03534 *Pseudomonas aeruginosa* PAO1, gi 13423604: AAK24088 *Caulobacter crescentus* CB15 Structural model of the RCL substrate binding site based on the catalytic active site of *L. leichmannii* N-deoxyribosyltransferase. Amino acid changes in RCL are indicated by an arrow. (amino acid numbers of *L. leichmannii* N-deoxyribosyltransferase have been modified in order to fit with the numbers of the alignment).

FIG. 4. Formation of Hypoxanthine following incubation of RCL with deoxyinosine 5'-monophosphate. A: HPLC chromatogram of deoxyinosine 5'-monophosphate (dIMP), B: HPLC chromatogram of hypoxanthine (Hx), C: HPLC chromatogram of deoxyinosine (dI), D: HPLC chromatogram of RCL assay products with deoxyinosine 5'-monophosphate as substrate. Retention times are indicated besides each peak. E and F correspond to the UV spectra from 210 to 400 nm of the hypoxanthine peak of panel B and of the product of the reaction from panel D respectively (indicated by an asterisk).

FIG. 8. Alignment of the rcl cluster (SEQ ID NOS:6, 8, 10, 24, 26, 28 and 30). Amino acids that participate in the catalytic active site of rcl [Y, D; S, E and S are indicated in bold.

DETAILED DESCRIPTION OF THE PREFERRED EMBODIMENTS

Figure 2:
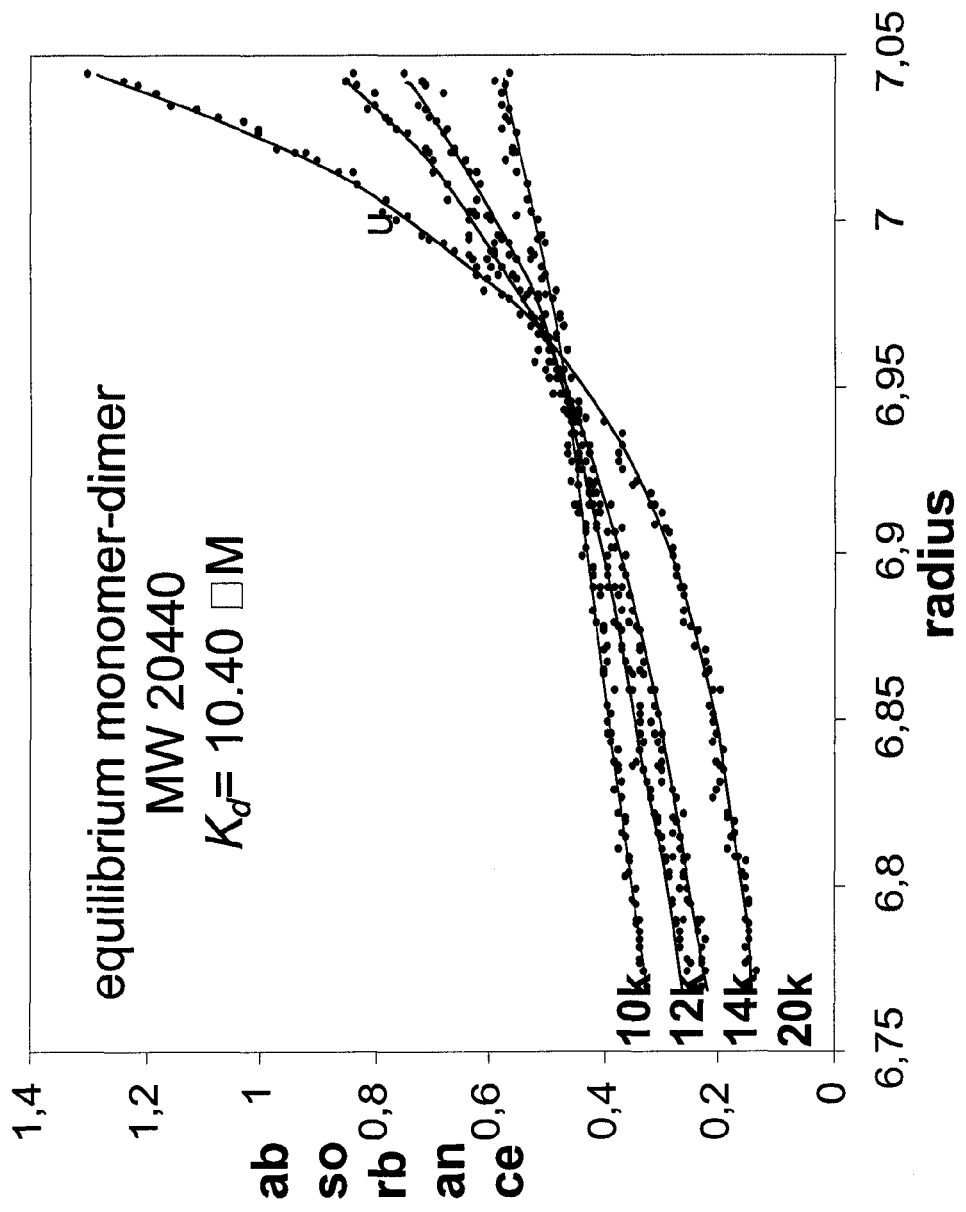
FIG. 2. Determination of the molecular mass of His-RCL by analytical ultracentrifugation. Absorbance scans from ultracentrifugation experiments were reported as a function of radius to the rotor center. Only one scan per speed (10 k, 12 k, 14 k, 20 krpm) and per starting RCL concentration (10 μM) was indicated for clarity. The best overall fit over 1706 points (three scans, five speeds) was fitted with the continuous lines corresponding to the monomer-dimer equilibrium with a $K_d=10.40$ μM and a variance of $4.76 \cdot 10^{-4}$. Residual values were below $10^{-2}$ evenly spreaded over best fit lines.

RCL is a c-Myc target with tumorigenic potential. Genome annotation predicted that RCL belong to the N-deoxyribosyltransferase family. However, its loose relationship to this class of enzymes did not allow to predict its precise biochemical function. The recombinant rat RCL protein expressed in *Escherichia coli* was purified either in its native form or with an N-terminal His-tag. Both proteins exhibit the same enzyme activity: deoxynucleoside 5'-monophosphate N-glycosidase, never described before, using dGMP being as the best substrate. RCL opens a new route in the nucleotide catabolic pathways by cleaving the N-glycosidic bond of deoxynucleoside 5'-monophosphates, to yield two reaction products, deoxyribose-5-phosphate and purine or pyrimidine base. Biochemical studies show marked differences in terms of the structure and catalytic mechanism between RCL and of its closest enzyme family neighbor, N-deoxyribosyltransferase. The reaction products of this novel enzyme activity have been implicated in purine or pyrimidine salvage, glycolysis and angiogenesis, and hence are all highly relevant for tumorigenesis.

Therefore, one embodiment of the present invention is to screen for agents that inhibit the activity of rcl, and particularly, its deoxynucleoside 5'monophosphate N-glycosidase activity. In another embodiment, the screening can be extended to identify agents that have anti-tumor effects and/or anti-angiogenesis effects.

One embodiment of the present invention is to screen for substances that inhibit the activity of rcl proteins described herein. Substances that inhibit the activity of rcl can, in turn, be screened for their capacity to inhibit tumor growth and/or promote tumor regression. Substances that inhibit the activity of rcl may also be used to screen for angiogenesis inhibition properties as well.

In one embodiment, screening of such substances that inhibit rcl deoxynucleoside 5'-monophosphate N-glycosidase activity can be performed by contacting the isolated polypeptide having the deoxynucleoside 5'-monophosphate N-glycosidase activity in a reaction vessel, e.g., a test tube, and comparing the activity of the contacted sample relative to a similar sample to which the substance has not been added. Of course, a measurable decrease in activity of the test sample is indicative of the capacity of the substance to inhibit rcl deoxynucleoside 5'-monophosphate N-glycosidase activity.

In another embodiment, cells transiently or stably expressing the rcl deoxynucleoside 5'-monophosphate N-glycosidase activity can be used to screen. In one aspect of this embodiment, expression of the polypeptide having deoxynucleoside 5'-monophosphate N-glycosidase activity is accomplished by providing an expression vehicle including transcriptional control regions as well as the coding sequence of the polypeptide having deoxynucleoside 5'-monophosphate N-glycosidase activity. Vehicles or vectors for transiently and/or stably expressing a particular nucleotide sequence are well-known in the field. In addition, the methodologies associated with introducing and causing expression of the coding nucleotide sequences are also well-known. The transcriptional control region can be a constitutive or inducible under certain controlled conditions, e.g., heat, chemical agents, and/or cell cycle to name a few.

In another embodiment, the cells used to screen the substances already express rcl deoxynucleoside 5'-monophosphate N-glycosidase activity and may be induced and/or cultured under certain conditions that cause an increased expression of the deoxynucleoside 5'-monophosphate N-glycosidase activity when compared to being cultured under normal conditions.

In preferred embodiments, the cells are mammalian cells, such as human and mouse cells.

With the cells in hand, the method of screening for substances can comprise contacting the cell expressing the deoxynucleoside 5'-monophosphate N-glycosidase activity described herein, measuring the deoxynucleoside 5'-monophosphate N-glycosidase activity and comparing the activity of cell prior to contacting or in a control cell that has not been contacted with the substance. A change in relative activity deoxynucleoside 5'-monophosphate N-glycosidase activity indicates that the substance is effective in inhibiting rcl deoxynucleoside 5'-monophosphate N-glycosidase activity.

In addition to or alternative to measuring enzymatic activity, assessment of inhibition of rcl can be performed by assaying the protein itself (by Western blotting, ELISA, RIA, and other techniques known to one skilled in the art), by assaying the mRNA encoding the protein (such as quantitative PCR, Northern blotting, RNAse protection assay, RNA dot-blotting, and other techniques known to one skilled in the art), or by assaying the activity of the regulatory elements. Preferably, the activity of regulatory elements can be assessed by reporter constructs consisting of DNA segments from the promoter, enhancer, and/or intronic elements coupled to cDNAs encoding reporters (such as luciferase, beta-galactosidase, green fluorescent protein, or other reporting genes that can be easily assayed). These reporter constructs can be transfected into cells, either stably, or transiently.

Identified substances can be further validated by giving the substance to an animal, and measuring as discussed above.

In another embodiment, the substances identified above, can be tested for anti-tumor activity, for example, inhibiting growth, metastasis, and/or stimulating tumor regression. It is understood that the spatial or timeframes in which the deoxynucleoside 5'-monophosphate N-glycosidase inhibition activity and antitumor activity can vary depending on the type and extent of testing. In particular, the time between testing deoxynucleoside 5'-monophosphate N-glycosidase inhibitory activity and antitumor activity can be hours, days, months or even years and can be performed by the same person or persons or different people. In addition, the deoxynucleoside 5'-monophosphate N-glycosidase inhibition screening can be performed at one location and the antitumor (or angiogenesis inhibition discussed below) can be performed at another location, e.g., different facilities, labs, cities, counties, states, and countries.

The method can utilize known animal models in which tumors can be induced and/or introduced. The substance identified as having deoxynucleoside 5'-monophosphate N-glycosidase inhibitory activity can be administered to the animal tumor model, e.g. a mouse, directly at the site of tumor growth, proximate to the tumor site, and/or other introduction methods known in the art, e.g., intravenously, intra-arterially, etc. The effect on tumor size, progression and/or regression can then be measured and compared to the tumor in the same animal prior to the administration of the substance and/or compared to a similar animal having a similar tumor but in which the substance had not been administered. A difference in size, properties or other known indicia of antitumor effects is indicative that the substance being screened has antitumor activity.

In another embodiment, the substances identified as having deoxynucleoside 5'-monophosphate N-glycosidase inhibitory activity can be tested for its capacity to inhibit angiogenesis, for example, inhibiting vascularization of an existing tumor. The method can utilize known animal models for assessing angiogenesis and/or in animal models in which tumors can be induced and/or introduced. The substance identified as having deoxynucleoside 5'-monophosphate N-glycosidase inhibitory activity can be administered to the animal tumor model, e.g. a mouse, directly at the site of tumor growth, proximate to the tumor site, and/or other introduction methods known in the art, e.g., intravenously, intra-arterially, etc. The effect on vascularization of a particular site, e.g., tumor and/or tumor size, progression and/or regression can then be measured and compared to the vascularization in the same animal prior to the administration of the substance and/or compared to a similar animal in which the substance had not been administered. A difference in vascularization, size, properties or other known indicia of angiogenesis effects is indicative that the substance being screened has anti-angiogenesis activity. In one embodiment, the inhibition of angiogenesis can be assessed by measuring the effects of the compound on specific proteins that are known to and/or are believed to be directly involved in angiogenesis (e.g., see Folkman, Annual Review of Medicine Vol. 57: 1-18 (February 2006). For example, in addition to or alternative to testing for vascularization directly in an animal, the substances can be tested for inhibition of extracellular matrix (ECM) formation or remodeling such as inhibition of matrix metalloproteinases, inhibition of uPA, inhibition of Collagenase, inhibitor of αvβ3 integrin adhesion receptor, inhibition of adhesion molecules, inhibition of angiogenic mediators and/or their receptors such as FGF-2, VEGF, PDGF, COX, etc, and/or inhibition of intracellular signaling.

The substance(s) identified above can be synthesized by any chemical or biological method and may be antibodies, antibody fragments, peptides, polypeptides, proteins, and/or other organic molecules synthesized and/or isolated from natural sources.

The substance(s) identified above can be prepared in a formulation containing one or more known physiologically acceptable diluents and/or carriers. The substance can also be used or administered to a mammalian subject in need of antitumor therapy, e.g. a human subject.

These methods can also be performed using high-throughput screening methodologies to enhance the speed at which the substances are identified and/or validated.

The Rcl protein and its nucleotide coding sequences from various species are known as shown below:

*Homo sapiens* (Lewis et al Mol. Cell. Biol. 17 (9), 4967-4978 (1997)) GenBank accession AAB96766

(SEQ ID NO:5)
```
  1 atggctgctg ccatggtgcc ggggcgcagc gagagctggg agcgcgggga gcctggccgc
 61 ccggccctgt acttctgcgg gagcattcgc ggcggacgcg aggacaggac gctgtacgag
121 cggatcgtgt ctcggctgcg gcgattcggg acagtgctca ccgagcacgt ggcggccgcc
181 gagctgggcg cgcgcgggga gaggctgctg gggggtgaca ggctcatcca tgagcaggac
241 ctggagtggc tgcagcaggc ggacgtggtc gtggcagaag tgacacagcc atccttgggt
301 gtaggctatg agctgggccg ggccgtggcc tttaacaagc ggatcctgtg cctgttccgc
361 ccgcagtctg gccgcgtgct ttcggccatg atccggggag cagcagatgg ctctcggttc
421 caggtgtggg actatgagga gggagaggtg gaggccctgc tggatcgata cttcgaggct
481 gatcctccag gcaggtggc tgcctcccct gacccaacca cttga
```

(SEQ ID NO: 6)
```
  1 maaamvpgrs eswergepgr palyfcgsir ggredrtlye rivsrlrrfg tvltehvaaa
 61 elgargeeaa ggdrliheqd lewlqqadvv vaevtqpslg vgyelgrava fnkrilclfr
121 pqsgrvlsam irgaadgsrf qvwdyeegev ealldryfea dppgqvaasp dptt
```

*Rattus norvegicus* (Lewis et al Mol. Cell. Biol. 17 (9), 4967-4978 (1997)) GenBank accession AAB95314

(SEQ ID NO:7)
```
  1 atggcggcat ccggggagca ggctccatgc tccgtgtact tctgcgggag catccgcggc
 61 gggcgcgagg accaagcact gtatgcgcgg atcgtgtcgc ggctccgacg ctatgggaag
121 gtgctcactg agcacgtggc tgatgctgag ttggagccgc ttggggaaga ggctgctggg
181 ggtgaccagt tcatccatga gcaggacctg aactggctgc agcaagcaga tgtggtagtg
241 gcggaagtga cacagccatc cttgggtgtt ggctatgaac tgggccgggc agtagctctt
301 gggaagccaa ttctgtgcct gtttcgacca cagtctggcc gagtgctttc cgccatgatc
361 cgcggagcag cagatggctc gaggttccag gtatgggact acgcagaagg agaagtggag
421 accatgctcg atcggtactt tgaggcatat cttcctcaga gacggcttc ctccagtcac
481 ccaagtgcct ga
```

(SEQ ID NO:8)
```
  1 maasgeqapc svyfcgsirg gredqalyar ivsrlrrygk vltehvadae leplgeeaag
 61 gdqfiheqdl nwlqqadvvv aevtqpslgv gyelgraval gkpilclfrp qsgrvlsami
121 rgaadgsrfq vwdyaegeve tmldryfeay lpqktassssh psa
```

*Mus musculus* (GenBank accession NM_207161)

(SEQ ID NO:9)
```
  1 atggcggcat ccggggagct ggttccatgc tctgtgtact tctgcgggag catccgcggc
 61 gggcgggaag accaagctct gtattcgcgg atcgtatccc ggctgcggcg ctatgggaag
121 gtgctcactg agcacgtggc tgatgctgag ttggagccgc gtggggaaga ggctgctggg
181 ggcgaccagt tcatccatga gcgggacctg gcctggctcc ggcaggccga tgtggtcgtg
241 gcagaagtga cacagccatc cttgggtgtt ggctacgaat gggccgggc agtagctctt
301 ggtaagccga tcctgtgcct gttccgacca cagtctggcc gagtgctttc cgccatgatc
```

-continued

```
361 cggggagcag ccgatggctc gaggttccag gtgtgggact acgcagagga agaagtggag
421 accatgctcc atcggtactt tgaggcttat cttcctcagg ggacggcttc ctccagtaac
481 ccaagtgcct gtcttaaccc tactgtatta gaaaaaattt aa
```

(SEQ ID NO:10)
```
  1 maasgelvpc svyfcgsirg gredqalysr ivsrlrrygk vltehvadae leprgeeaag
 61 gdqfiherdl awlrqadvvv aevtqpslgv gyelgraval gkpilclfrp qsgrvlsami
121 rgaadgsrfq vwdyaeeeve tmlhryfeay lpqgtasssn psaclnptvl eki.
```

*Canis familiaris* (Gen Bank accession XM_538931

(SEQ ID NO: 23)
```
  1 cggcggcggg gatgtcgggg atggcggcgg cggcggccgg agcgcgggag cgcagggagc
 61 cgggccagcc gggccagccg ggccgccgag cgctgtactt ctgcgggagc gtccgcggcg
121 gccgcgagga ccgggcgctg tacgggagga tcgtgtcgcg gctgcggcgc ttcggggcgg
181 tgctcacgga gcacgtggcg gccgccgagc tgggcgcgcg cggggaagag gctgctgggg
241 gcgacaggtt catctacgag cgggacctgg cttggctgca gcaggcagat gtggtggtgg
301 cagaagtgac ccagccatcg ttgggcgtgg gctatgagct gggccaggcc atggccctca
361 ataagcggat cttgtgcctc ttccgtccgc agtctggccg agtgctttca gccatgatcc
421 ggggagcggc agacggctca aggttccagg tgttggacta tgaagagggc caggtggagg
481 ccatgctgga tcaatacttt gaggctgacc ctccctagca ggtggctgcc tccctgacc
541 caactgcttg ccttagcccc actttgttaa ttcttctaat cccagactct tagtaccctt
```

(SEQ ID NO:24)
```
  1 maaaaagare rrepgqpgqp grralyfcgs vrggredral ygrivsrlrr fgavltehva
 61 aaelgargee aaggdrfiye rdlawlqqad vvvaevtqps lgvgyelgqa malnkrilcl
121 frpqsgrvls amirgaadgs rfqvldyeeg qveamldqyf eadp
```

*Equus caballus* (GenBank Accession XM_001497421

(SEQ ID NO:25)
```
  1 atggcggcga cgatggccgc agcgcgcgag cgcggggagc cgggccgcag ggccctgtac
 61 ttctgcggga gcatccgcgg cggacgcgac gaccgggcgc tgtacaagcg gatcgtgtcg
121 cggctgcggc gcttcgggac cgtgctcacc gagtacgtgg cggctcccga cctgggggaa
181 gaggctgctg ggggtgacaa gctcatccat gagcgagacc tggcctggct gcagcaggct
241 gatgtggtcg tggcagaagt gacccagcca tccttgggtg taggctacga gctgggccgg
301 gccgtagccc tcaataagcg aatcctgtgc ctcttccgcc cgcagtctgg ccgagtgctt
361 tcagccatga tccgcggagc agcagatggc ttgcggttcc aggtatggga ctatgaagag
421 ggagaggtgg aggccatgct ggatcgatac tttgaggctg atccttctga ggaggtggct
481 gcctcccctg agccaaccgc ttga
```

(SEQ ID NO:26)
```
  1 maatmaaare rgepgrraly fcgsirggrd dralykrivs rlrrfgtvlt eyvaapdlge
 61 eaaggdklih erdlawlqqa dvvvaevtqp slgvgyelgr avalnkrilc lfrpqsgrvl
121 samirgaadg lrfqvwdyee geveamldry feadpseeva aspepta
```

*Bos Taurus* (GenBank Accession XM_864815)

(SEQ ID NO:27)
```
  1 ccggcggggc ctgcggggcc cgggatggcg gcggcggcgg cggctggaac cgtggatccg
 61 ggtcgtctct ccctgtactt ctgcgggagt atccgtggcg gacgcgagga tcgggaactg
121 tacgtgcgca tcgtgtctcg cctccggcgc ttcggggtgg tgcttaccga gcatgtggcg
181 gccgccgagg tggacgagag cggggaagag gctgctggag gcgacaagct catccatgat
241 cgggacctgg cctggctgca gcaggcagat gtggtcgtgg cagaagtgac ccagccctct
301 ctgggggtag gctatgagct gggccgggcc gtagccctcc acaaacoagt cctgtgcctg
361 tttcgcccaa agtctggccg agtgctctca gccatgatcc ggggagcagc caatggctcc
421 aggttccagg ttccaggtgt gggactacga ggaagcagaa gtggaggccc tgctagatcg
481 gtactttgag gcgtatcctc ctgagcaggt ggctgcctct cctgacccaa cagcttgact
541 tcaccccagt ttttattaaa ttctcctgat c
```

(SEQ ID NO:28)
```
  1 maaaaaagtv dpgrlslyfc gsirggredr elyvrivsrl rrfgvvlteh vaaaevdesg
 61 eeaaggdkli hdrdlawlqq advvvaevtq pslgvgyelg ravalhkpvl clfrpksgrv
121 lsamirgaan gsrfqvpgvg lrgsrsggpa rsvl
```

*Danio rerio* (GenBank Accession XM_685209)

(SEQ ID NO:29)
```
  1 gcagtttatc tgaacttccc gtgaatgctg tgctgctgag aaaagcacgc ttgtatcaca
 61 gaagaaagac gaggactcct gcaaattatg aacatatact tttgcggaag cattcgggga
121 gggcgacagg acgtggttat ttatcagaca atagtgaaga agttgcagca gtatggcaat
181 gttttaaccg agcatgtgag ttatgacagc ctgtctgaca agggtgaaga taaagatgga
241 gataaagcca ttcatgatcg ggatgtgcag tggctgacga tgtctgacgt gatagtagca
301 gaagtgacgc agccatcttt aggtgttggt tatgaactgg gccgagctgt ggcaatgaac
361 aagaggatcc tctgtctctt cagaccttt tctggaaaag tgctctccgc catgatcaga
421 ggagcgtcag ccaaaccact cttccaagta caagactaca agaggacga agtggagaac
481 atcttggagg aatattttga gactctcact aagaactgat gagcagctga tcataacaaa
541 tcctatgtgc tgctcttatt caaatcaaca ggactgcttt ggtaagcatt tgtagtgaaa
601 atgcatatta agcatacaca gtgtattgtt acttgctctt gaataaatct ggttttgtta
661 acaaca
```

(SEQ ID NO:30)
```
  1 mniyfcgsir ggrqdvviyq tivkklqqyg nvltehvsyd slsdkgedkd gdkaihdrdv
 61 qwltmsdviv aevtqpslgv gyelgravam nkrilclfrp fsgkvlsami rgasakplfq
121 vqdykedeve nileeyfetl tkn
```

The rcl that can be employed in the inventive methods described herein are those full length coding sequences, protein sequences, and as well as functional variants, chimeric proteins, muteins, and mimetics of these. In another embodiment, the rcl that can be used are those that are encoded by polynucleotide sequence with at least 90%, 95, 97, 98 and/or 99% identity to the wildtype full-length human and/or mouse rcl coding sequence, these polynucleotides will hybridize under stringent conditions to the coding polynucleotide sequence of the wild-type full length sequences. The terms "stringent conditions" or "stringent hybridization conditions" includes reference to conditions under which a polynucleotide will hybridize to its target sequence, to a detectably greater degree than other sequences (e.g., at least 2-fold over background). Stringent conditions will be those in which hybridization in 50% formamide, 1 M NaCl, 1% SDS at 37° C., and a wash in 0.1×SSC at 60 to 65° C. is performed. Amino acid and polynucleotide identity, homology and/or similarity can be determined using the ClustalW algorithm, MEGALIGN™, Lasergene, Wis.)

Examples of the various rcl functional variants, muteins, and mimetics include functional fragments and variants (e.g., structurally and biologically similar to the wild-type protein and having at least one biologically equivalent domain), chemical derivatives (e.g., containing additional chemical moieties, such as polyethyleneglycol and polyethyleneglycol derivatives thereof, and/or glycosylated forms), and peptidomimetics (e.g., a low molecular weight compound that mimics a peptide in structure and/or function (see, e.g., Abell, Advances in Amino Acid Mimetics and Peptidomimetics, London: JAI Press (1997); Gante, Peptidmimetica—massgeschneiderte Enzyminhibitoren Angew. Chem. 106: 1780-1802 (1994); and Olson et al., J. Med. Chem. 36: 3039-3049 (1993)).

The various functional derivatives, variants, muteins and/or mimetics of rcl preferably retain at least 20%, preferably 50%, more preferably at least 75% and/or most preferably at least 90% of the biological activity of wild-type human and/or mouse rcl activity—the amount of biological activity include 25%, 30%, 35%, 40%, 45%, 55%, 60%, 65%, 70%, 75%, 80%, 85%, 95%; and all values and subranges there between. Furthermore, the functional derivatives, variants, muteins and/or mimetics of rcl can also have 100% or more of the biological activity relative to wild-type human and/or mouse rcl activity—the amount of biological activity including at least 105%, at least 110%, at least 125%, at least 150%, and at least 200%. Preferably, the functional derivatives, variants, muteins and/or mimetics of rcl retain the glutamic acid (E) at position 93 of the mouse RCL sequence (SEQ ID No.:10) and in another embodiment, also include the catalytic site structure shown in FIG. 3, and corresponding to aminoacids Y13, D69, S87, E93 and S117 [RCL rat numbering: SEQ ID No.:8)

Figure 6:
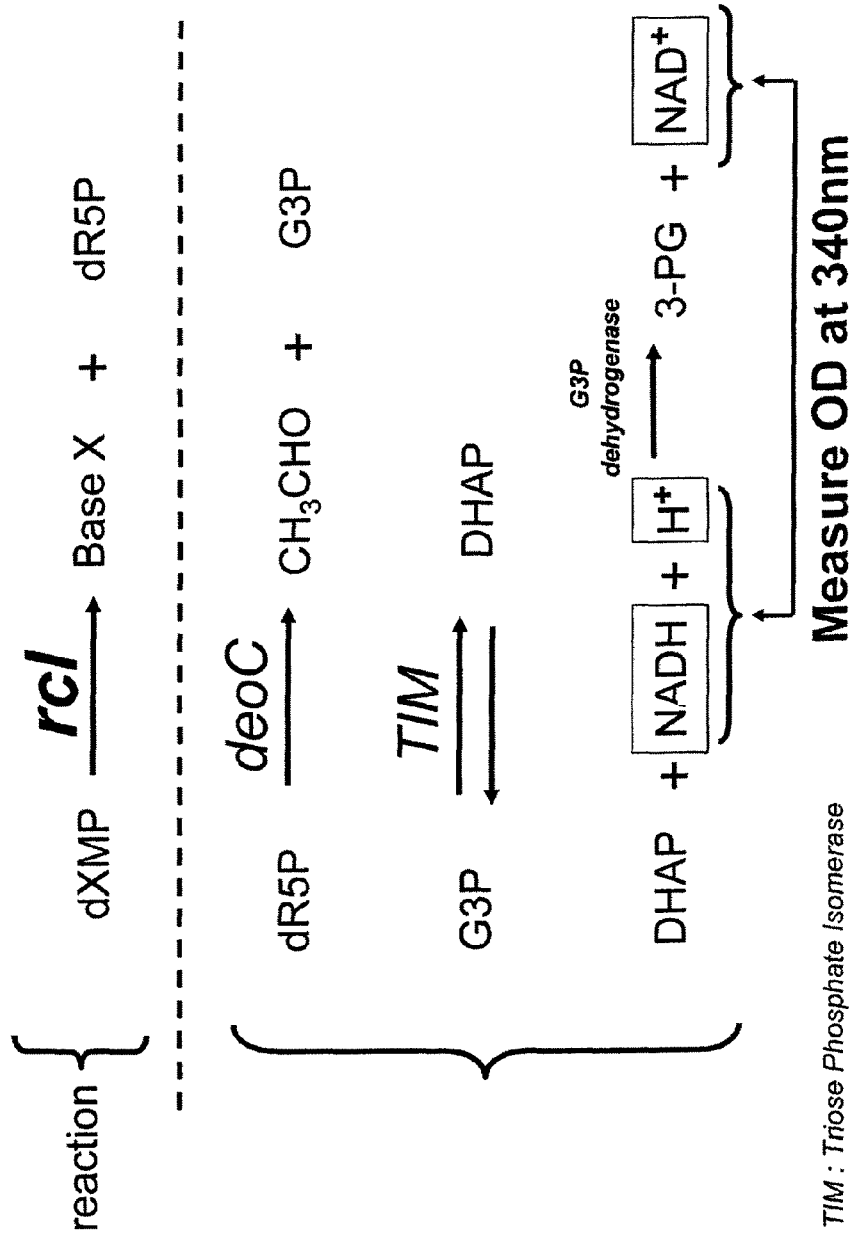
FIG. 6 A schematic diagram for measuring deoxynucleoside 5'monophosphate N-glycosidase catalytic activity.

To measure the biological activity of rcl, the methods described herein can be used, e.g., measuring deoxynucleoside 5'-monophosphate N-glycosidase. In one embodiment, this can be done following the schematic illustrated in FIG. 6 by coupling two enzymatic activities, that of RCL (deoxynucleoside 5'-monophosphate N-glycosidase) and that of the Glycerol 3 phosphate dehydrogenase (G3P). In this embodiment:

1—RCL Reaction

The RCL catalyses the transformation of desoxynucleoside mono phosphate (dXMP) leading to (desoxyribose 5 phosphate) dR5P, the substrate of the deoxyribose-phosphate aldolase (DeoC).

2—Dosage

First Step

Under the action of DeoC, dR5P will be transformed in acetaldehyde (CH3CHO)+glyceraldehyde 3 phosphate (G3P).

Second Step

Under the catalytic action of the Triose Phosphatase Isomerase (TIM), the G3P will be transformed into dihydroacetone phosphate (DHAP).

Third Step

The DHAP, under the action of glycerol 3 phosphate dehydrogenase (G3P) will be transformed in 3 phospho glycerate (3-PG), in the presence of the cofactor NADH which present absorption at 340 nm, allowing the measurement of the reaction.

EXAMPLES

Example 1

Experimental Procedures

Chemicals

Ribonucleosides and deoxyribonucleosides, mono-, di- and triphosphate derivatives of adenine, cytosine, guanine, hypoxanthine, thymine and uracil were from SIGMA-ALDRICH.

6-methylthio-guanosine 5'-monophosphate, 2'-deoxyguanosine 3'-monophosphate and 8-oxo-deoxyguanosine 5'-monophosphate were from Jena Bioscience.

Overexpression and Purification of RCL and of the N-Terminal His-Tagged Rcl

The Rcl cDNA cloned into pCR2.1 as a NcoI-BamHI fragment was subcloned into pET24d digested with the same restriction enzymes. The resulting pET24Rcl was used to transform strain Bli5 (BL21 (DE3) pDIA 17). One liter of LB medium supplemented with 50 μg/ml of chloramphenicol and kanamycin was inoculated with an overnight culture of Bli5 containing pET24dRcl. The culture was grown under agitation at 37° C. until an $OD_{600}$ of 0.8. Isopropyl-1-thio-beta-D-galactopyranoside (IPTG) was added to a final concentration of 1 mM, and the cultures further incubated for 3 h. Bacteria were harvested by centrifugation at 4500 g for 20 min at 4° C., and the pellet frozen at −20° C. Cells were resuspended in 35 ml of 50 mM Tris pH 7.5 and broken by two passages through a French press at 14000 p.s.i. The lysate was centrifuged at 25000 g for 30 min at 4° C. The supernatant was loaded on a Q-fast flow column previously equilibrated with the same buffer. Proteins were eluted with a 0-40% NaCl gradient. RCL was eluted between 20 and 25% NaCl, and the corresponding fractions were pooled and precipitated with solid ammonium sulfate. Pelleted RCL was resuspended in Tris 50 mM pH 7.5 and further purified by filtration on a Sephacryl S-200 column previously equilibrated with the same buffer. The elution was followed by UV absorption at 280 nm, and each fraction was analyzed by SDS-PAGE electrophoresis and N-glycosidase activity. The purest and most active fractions were concentrated on an Omega cell 10K membrane (Pall) and stored at −20° C.

The N-terminal His tagged RCL was overproduced and purified as follows:

The Rcl gene cloned into pCR2.1 as a NdeI-BamHI fragment was subcloned into pET28a digested with the same restriction enzymes. The resulting pET28aRcl was used to transform strain Bli5. Culture conditions and induction were performed as described above. Frozen cells resuspended in 40 ml of extraction/wash buffer (50 mM $Na_2HPO_4$, $NaH_2PO_4$, 300 mM NaCl pH 7.0) were broken by two passages through a French press at 14000 p.s.i. The lysate was centrifuged at 25000 g for 30 min at 4° C. The supernatant was loaded on a column containing 6 ml of TALON (BD Bioscience) resin previously equilibrated with the same buffer. After washing, RCL was eluted with 150 mM imidazole. Fractions containing RCL were pooled and concentrated on an Omega cell 10K membrane (Pall). The His-tagged RCL was further purified by gel filtration on a Sephacryl S-200 column. The purity was checked by SDS PAGE electrophoresis and by measuring the specific activity. Purified His-tagged RCL was stored at −20° C.

RCL with Glu-93 replaced by Ala (E93A mutant) by site directed mutagenesis

Oligonucleotides T7prom: 5'-CGCGAAATTAATAC-GACTCACTATAGGGG-3' (SEQ ID NO:1) and olinvE93A: 5'-GCCCGGCCCAGCGCATAGCCAACACCCAAG-3' (SEQ ID NO:2)

T7term: 5'-GGGGTTATGCTAGTTATTGCTCAGCGG-3' (SEQ ID NO:3) and olE93A 5'-CTTGGGTGTTGGCTAT-GCGCTGGGCCGGGC-3' (SEQ ID NO:4) were used in two separate PCR with plasmid pET28aRcl as DNA template. The parameters used were 1 cycle of 5 min at 95° C.; 25 cycles of 30 s at 95° C., 30 s at 51.5° C., and 1 min at 72° C.; and 1 cycle of 10 min at 72° C. An aliquot (1/100 of the reaction) of each PCR was used as DNA template in a third PCR with oligonucleotides T7prom and T7term. The parameters used were the same as described above. The PCR product was purified by using the QIAquick PCR purification kit (Qiagen) then digested with NdeI and BamHI enzymes over 2 h at 37° C. and re-purified. Each PCR product was ligated with plasmid pET28a digested with the same restriction enzymes. The ligation mixtures were used to transform strain DH5α. Plasmids with the correct sequence, pET28aRclE$_{93}$A, were used to transform strain Bli5.

Enzyme Activity Assays

The enzyme activity was determined either spectrophotometrically by following one of the reaction products, hypoxanthine or deoxyribose 5-phosphate, or by HPLC separation and UV detection of the released nucleobase and the remaining substrate.

a) dIMP was used as a substrate and the hypoxanthine released oxidized to uric acid by xanthine oxidase. The absorption increase at 290 nm was converted in enzymatic units using a millimolar absorbance coefficient of 12.0. One milliliter of the medium reaction thermostated at 37° C. contained 50 mM Tris-HCl pH 7.5, 1 mM dIMP, 0.2 units of xanthine oxidase (Roche Applied Sciences) and 50 to 200 μg of purified RCL.

b) D-glyceraldehyde-3-phosphate, which is produced by the deoxyribose 5-phosphate aldolase from deoxyribose 5-phosphate, was coupled to the oxidation of NADH to NAD via the reactions catalyzed by triose phosphate isomerase and glycerol 3-phosphate dehydrogenase. The decrease in absorbance at 340 nm was followed on a Amersham Biosciences Ultrospec 3100 pro spectrophotometer, using a millimolar absorbance coefficient of 6.22. The reaction medium (1 mL final volume) contained 50 mM Tris-acetate pH 6.0, 0.1 mM NADH, and 1.5 units of each glycerol-3-phosphate dehydrogenase, triose phosphate isomerase (Roche Applied Sciences), deoxyribose-5-phosphate aldolase* and 50 to 200 μg of purified RCL. One unit enzyme activity corresponds to 1 μmole product formed in 1 min at 37° C. and pH 6.0.

c) HPLC assays were as described previously (Kaminski, P. A. (2002) *J Biol Chem* 277, 14400-7) except that the reactions were performed at 37° C. in 50 mM Tris-HCl pH 7.5 containing 1 mM dNMP and the appropriate amount of purified RCL.

* Overproduction and purification of *E. coli* deoxyribose 5-phosphate aldolase

The NdeI-HindIII fragment of pHSP234 which contains the *E. coli* deoC gene (a kind gift of H. Sakamoto) was cloned into plasmid pET28a digested with the same restriction enzymes. The resulting plasmid, in strain Bli5, allows the expression of the deoxyribose-5-phosphate aldolase with an N-terminal His tag. Culture condition, induction, centrifugation, and purification on TALON resin were as described for His-RCL. Fractions containing deoxyribose-5-phosphate aldolase were dialyzed extensively against 10 mM Tris pH 7.5, 50 mM NaCl and 1 mM DTT, concentrated in an Omega cell 10K and kept frozen at −20° C.

Other Analytical Procedures

Protein concentration was determined using the Bradford assay kit from Biorad. SDS PAGE was performed as described by Laemmli (Laemmli, U. K. (1970) *Nature* 227, 680-5). Mass spectrometry was performed by the PT3 proteomique of the Pasteur Institute as previously described (Kaminski, P. A. (2002) *J Biol Chem* 277, 14400-7). Equilibrium sedimentation experiments were performed at 20° C. using a Beckman Optima XL-A analytical ultracentrifuge equipped with an An-60 Ti four-hole rotor. Samples (150 μl) at three protein concentrations (3 μM, 10 μM, 30 μM), in 20 mM Tris-HCl pH 7.5, 150 mM NaCl were run at six speeds (8, 10, 12, 14, 20 and 50krpm). Five profiles were recorded after reaching equilibrium (12-18 h) at three wavelengths according to sample concentration (291 nm, 280 nm, 231 nm respectively). Partial specific volume v-bar of 0.713 mL/g was computed from the amino acid composition; solvent density=1.004 g/mL and viscosity=1.03 cp were set from tables. Data analysis was performed with the program Origin (Microcal).

Results

Purification of RCL and Molecular Properties of the Recombinant Proteins

Both RCL and His-RCL were produced as soluble proteins and their purity estimated to be greater than 95% by SDS-PAGE (FIG. 1). The molecular mass of RCL and His-RCL according to appropriate markers (24-26 kDa) is higher than the deduced 18-20 kDa molecular mass. Electrospray ionization mass spectrometry indicated a molecular mass of His-RCL of 19812.06±1.72, very close to the sequence deduced one (19813.15) with the initiating methionine being deleted. Equilibrium sedimentation experiments showed that at 3 μM, His-RCL is mostly monomeric (free averaged molecular mass 22603). At 30 M, His-RCL is mostly dimeric (free averaged molecular mass 40522). At 10 μM, His-RCL is at equilibrium between monomeric (MW 20440) and dimeric (MW 40880) states (FIG. 2). The dissociation constant ($K_d$) computed from the best fit with the 30 μM and the 10 μM-datasets, was 9.53 μM and 10.40 μM, with a mean value 10±1 μM. No higher molecular mass oligomers were detected indicating that the quaternary structure of RCL differs from that of N-deoxyribosyltransferase which is a stable hexamer.

RCL at concentrations >1 mg/ml could be stored at −20° C. for at least 1 year without loss of activity. RCL is a heat stable protein as the temperature of half denaturation (Tm) was estimated to be around 74° C.

The Rationale for Identifying the Catalytic Function of RCL

Examination of the homology of RCL with N-deoxyribosyltransferase from lactobacilli revealed several interesting features (FIG. 3). Several amino acids that participate in the active site of *L. leichmannii* N-deoxyribosyltransferase are conserved in RCL, as the Glu 105 (corresponding to Glu 93 in RCL rat numbering) which is also involved in a hydrogen bond with the 3'-OH of the sugar of the deoxynucleoside (Armstrong et al (1996) *Structure* 4, 97-107). Tyr 2 (corresponding to Tyr 13 in RCL rat numbering) which stabilizes this bond as well as Asp 75 (corresponding to Asp 69 in RCL rat numbering) involved in the binding of the base are also conserved. Interestingly, the two amino acids, Asp 99 and Asn 172, involved in the binding of the 5'-OH of the sugar are not conserved in RCL being replaced by two Ser residues with smaller size (FIG. 3, inset) (Asp 99 replaced by serine corresponds to S87 according to RCL rat numbering and Asn 172 replaced by serine corresponds to S117 according to RCL rat numbering). We hypothesized that the substrate recognized by RCL should be related to deoxynucleosides (substrate of N-deoxyribosyltransferase) or the corresponding phosphorylated compounds. Consequently, approximately 50 ribonucleosides and deoxyribonucleosides including their mono-, di-, and triphosphate derivatives were incubated for several hours with pure RCL, then the reaction products were analyzed by thin layer chromatography and later by HPLC (FIG. 4). When RCL was incubated with various deoxyribonucleoside 5'-monophosphates (and to a lesser extent with deoxyribonucleoside diphosphates), a constant reaction product was the corresponding free base. We deduced that RCL catalyzes the following hydrolytic reaction: deoxyribonucleoside 5'-monophosphate (dNMP)+H2O→free base (N)+deoxyribose 5-phosphate (dR5P). The existence of the two reaction products in stoichiometric amounts was demonstrated by using dIMP as a substrate and identifying enzymatically the end products, hypoxanthine and deoxyribose 5-phosphate as described under experimental procedures. No deoxyribose 5-phosphate transfer was detected, whether dNMP was the donor or any base as acceptor. In addition, no dNMP was synthesized when RCL was incubated in the presence of deoxyribose 5-phosphate and a base (data not shown). We conclude that RCL cleaves the N-glycosidic bond of deoxynucleoside 5'-monophosphate to liberate deoxyribose 5-phosphate and the free base and that this reaction is not reversible, Hence, we found a previously un-described enzyme, deoxynucleoside 5'-monophoshate N-glycosidase, that is encoded by Rcl, a Myc target with tumorigenic potential.

Catalytic properties of the recombinant proteins. With saturating concentrations of dGMP or dCMP, RCL showed an optimum around pH 6.0. 50% of the maximal activity was still observed at pH 7.0 in the case of dCMP while it was only 20% in the case of dGMP. In both cases at pH 8.0, only 10% of the enzyme activity remained. Several metals were tested for their ability to stimulate or inhibit the reaction: $Ca^{2+}$, $Mg^{2+}$, $Zn^{2+}$, $Na^+$, and $K^+$. Only $Zn^{2+}$ inhibits the reaction, while the other metals have no effect.

Initial velocity experiments were carried out at variable concentrations of the six deoxynucleoside 5'-monophosphate: dAMP, dCMP, dGMP, dIMP, dTMP and dUMP (Table 1). The kinetic parameters with dGMP indicates that RCL is a typical Michaelian enzyme with a $K_m$ of 50 μM and a $V_{max}$ of 0.09 U. $mg^{-1}$ which corresponds to a $k_{cat}$ of 0.0268 $s^{-1}$. Purine deoxynucleotides have a better affinity for RCL than pyrimidine deoxynucleotides. The $K_m$ of RCL for dCMP (4 mM), dUMP (15 mM) and dTMP (>50 mM) are high as compared with dGMP (50 μM), dAMP (250 μM) and dIMP (450 μM). The $k_{cat}/K_m$ measure of substrate efficiency also indicates a preference for purine deoxynucleotides. RCL cleaves dGMP 20 times more efficiently than dAMP and 40 times than dIMP.

TABLE 1

Kinetic parameters of His-RCL with different dNMPs as substrate. $V_{max}$ and $K_m$ were obtained from double reciprocal plots of initial velocity measurements. For each dNMPs five different concentrations were used.

| Nucleotide | $k_{cat}$ ($s^{-1}$) | $K_m$ (μM) | $k_{cat}/K_m$ ($M^{-1} \cdot s^{-1}$) |
|---|---|---|---|
| dGMP | 0.0297 | 48 | 619 |
| dAMP | 0.0066 | 250 | 26.4 |
| dIMP | 0.0066 | 450 | 14.7 |
| dCMP | 0.0231 | 4000 | 5.8 |
| dUMP | 0.158 | 15600 | 10.1 |
| dTMP | ND | ND | <0.14 |

ND: not determined $K_m$ << [dTMP]

In order to better understand the catalytic mechanism of RCL, several compounds were tested as substrate or inhibitor of the enzyme activity. The initial velocity of the reaction was measured either at variable concentration of dGMP both in the absence and presence of inhibitors, or at fixed concentration of dGMP and variable concentrations of inhibitors allowing the testing of the nature of the inhibition. The double reciprocal plot confirms that GMP and 6-methylthio-GMP are competitive inhibitors for dGMP with a $K_i$ of 20 μM and 10 μM, respectively. Thus, the presence of an OH at the 2' position of the sugar has a critical influence. The position of the phosphate is also important as 2'-deoxyguanosine 3'-monophosphate is neither a substrate nor an inhibitor of RCL. The presence of an oxo at position 8 of the base is sufficient to modify the recognition by RCL, as 8-oxo-dGMP is neither a substrate nor an inhibitor.

Kinetic parameters of RCL $E_{93}A$ $Y_{13}A$, $D_{69}A$, $S_{87}D$, and $S_{117}N$ mutants The similarity of amino acids sequence and the similarity of reaction between RCL and NDT lead us to investigate the catalytic mechanism. The Glu-93 was chosen for site directed mutagenesis because it corresponds to Glu-105 in the active site nucleophile in *L. leichmannii* N-deoxyribosyltransferase (Armstrong, et al (1996) *Structure* 4, 97-107; Porter, et al (1995) *J Biol Chem* 270, 15551-6) and its conservation in the different N-deoxyribosyltransferase-like sequences (FIG. 3). The inventors showed that the mutations introduced at Tyr-13, Asp-69, Ser-87 or Ser-117 have a profound effect on the Km (Table 2). It appears clearly that both serines, Ser-87 and Ser-117 are implicated in catalytic activity. The Km for mutated S117N is enhanced of a factor of 450 and for S87D the $K_m$ is enhanced of a factor of 600. The Glu-93 mutated to Ala in RCL has also an effect on the $K_m$ that is enhanced by a factor of 170 while the $V_{max}$ remains in the same order of magnitude. It was thus concluded that Glu-93 may be involved in the substrate binding but is not the catalytic amino acid as found in *L. leichmannii* N-deoxyribosyltransferase

TABLE 2

Kinetic parameters of His-RCL (wild-type) and mutants His-RCL $E_{93}A$, $Y_{13}A$, $D_{69}A$, $S_{87}D$, or $S_{117}N$ with dGMP as substrate. dGMP concentrations vary from 250 μM to 20 mM. $V_{max}$ and $K_m$ were obtained from double reciprocal plots of initial velocity measurements.

| Enzyme | $k_{cat}/K_m$ in $M^{-1} \cdot s^{-1}$ | $K_m$ in μM | $k_{cat}$ $s^{-1}$ |
|---|---|---|---|
| Wt | 621 | 48 | 0.0298 |
| Y13A | 4.46 | 10000 | 0.0446 |
| D69A | 4.46 | 260 | 0.0171 |
| S87D | 6.43 | 32000 | 0.206 |
| E93A | 4.66 | 8500 | 0.0396 |
| S117D | 4.5 | 22000 | 0.099 |

TABLE 3

Kinetic parameters of His-RCL with additional indicated substrates

| Substrate | $k_{cat}$ | $K_m$ | $k_{cat}/K_m$ |
|---|---|---|---|
| dGMP | 0.033 | 77 ± 20 | 428 |
| 06-methyl-dGMP | 0.033 | 61 ± 16 | 536.6 |
| N7-methyl-dGMP | 2.376 | 470 ± 68 | 5055 |
| N2-ethyl-dGMP | 0.0528 | 71 ± 8 | 743.6 |
| Glyoxal-dGMP | 0.029 | 192 ± 7 | 151 |

Discussion

With increasing numbers of genome sequences available, functional prediction of open reading frames is a significant advance, but it remains a challenge despite sequence homology to known functional domains. For example, the clustering of orthologous groups (COGs) that brought together comparative genomics and protein classification has allowed the automatic functional annotation of genes and proteins (Tatusov, et al (1997) *Science* 278, 631-7). Orthologs most often have equivalent functions, and COG 3613 illustrates all the proteins with a conserved domain with N-deoxyribosyltransferase. In COG 3613, only two crystal structures of N-deoxyribosyltransferases in the presence of different ligands were described (Armstrong, et al (1996) *Structure* 4, 97-107; Anand, et al (2004) *Biochemistry* 43, 2384-93). These structures allowed the determination of the amino acids residues important in substrate binding and catalysis, and also explained the substrate specificity. Knowing this, we reconsider the 3613 COG by focusing our interest on RCL. RCL was chosen for several reasons: i) it was the more distant protein in the COG, ii) its function was unknown, iii) it was only present in mammals and iv) the Rcl gene is a Myc target gene, which is up-regulated in human cancers and has tumorigenic potential. By combining the structural data obtained with *L. leichmannii* and *L. helveticus* N-deoxyribosyltransferases and the sequence identities of RCL and N-deoxyribosyltransferases, we hypothesized that the two proteins may have related activities with different substrate specificities. The biochemical experiments performed with either pure native RCL or with a His-tagged RCL demonstrate that it codes for a deoxynucleoside 5'-monophosphate glycosidase, a previously undescribed activity. Indeed, N-glycosylhydrolases with a pyrimidine preference have been described in *Neisseria meningitidis* (Jyssum, S. (1989) *Apmis* 97, 343-6), *Streptomyces virginiae* (Imada, A. (1967) *J. Gen. Appl. Microbiol.* 13, 267-278; Imada, et al (1967) *J. Gen. Appl. Microbiol.* 13, 255-265) and *Streptomyces griseochromogenes* (23, 24). On the other hand, ribosylhydrolases specific for inosine or adenosine 5'-monophosphate were also reported (Kuninaka, A. (1957) *Koso Kagaku Shinpojiumu* 12, 65; Leung, H. B. & Schramm, V. L. (1984) *J. Biol. Chem.* 259, 6972-6978). None of them hydrolyze purine deoxynucleoside 5'-monophosphate. The RCL activity is somehow related to N-deoxyribosyltransferase since, in the absence of an acceptor base, *L. leichmanni* N-deoxyribosyltransferase catalyzes the hydrolysis of deoxynucleosides (Smar, et al (1991) *Biochemistry* 30, 7908-12). *L. leichmanni* N-deoxyribosyltransferase is a hexamer in its native state with one active site per subunit. A complete catalytic center requires the participation from a neighbouring subunit indicating that oligomerization is necessary for catalysis (Armstrong, et al (1996) *Structure* 4, 97-107). Molecular mass measurement shows that RCL is in a monomer-dimer equilibrium. It is notable that RCL (C6orf108) also dimerizes intracellularly in the yeast two-hybrid assay (Lewis, et al (1997) *Mol Cell Biol* 17, 4967-78). Considering the RCL concentration used and the tendency of RCL to aggregate at high concentration, it is likely that RCL is active as a monomer in the catalysis conditions explored in vitro; however, whether its activity requires a dimeric state in vivo is not known. Thus, the quaternary structure of RCL should be different from that of *L. leichmannii* N-deoxyribosyltransferase, which exists as a hexamer.

The difference of substrate specificity, deoxynucleosides vs deoxynucleosides 5'-monophosphate, between N-deoxyribosyltransferase and RCL might be explained by the replacement of Asp 99 and Asn 172, involved in the binding of the 5'-OH of the sugar by two Ser that are smaller. This would allow more space for the phosphate group of dNMP. It was previously established that N-deoxyribosyltransferase mechanism is similar to that described for glycoside hydrolases involving a carboxyl group from an aspartyl or a glutamyl residue as the active site nucleophile (Armstrong, et al (1996) *Structure* 4, 97-107; Porter, et al (1995) *J Biol Chem* 270, 15551-6; Short, et al (1996) *J Biol Chem* 271, 4978-87). Conservation of the putative catalytic Glu was an indication of a similar mechanism for RCL. This hypothesis was further supported by the competitive inhibition of dGMP hydrolysis by GMP. However, site directed mutagenesis of Glu-93 to Ala modified the $K_m$ but not the $V_{max}$ which indicates that Glu-93 is important for the binding of the ligand but is not the active site nucleophile. Other putative catalytic residues are under investigation. In summary, the RCL and N-deoxyribosyltransferases identities appear to be limited to the deoxynucleoside binding since their structure, function and mechanism differ. As previously indicated, other crucial amino acids for catalytic activity of RCL are Y13, D69, S87 and S117 (RCL rat numbering). A Clustal alignment (FIG. 8) shows that RCL proteins are well conserved and that the amino acids implicated in their catalytic activity (in bold) are highly conserved.

Figure 5:
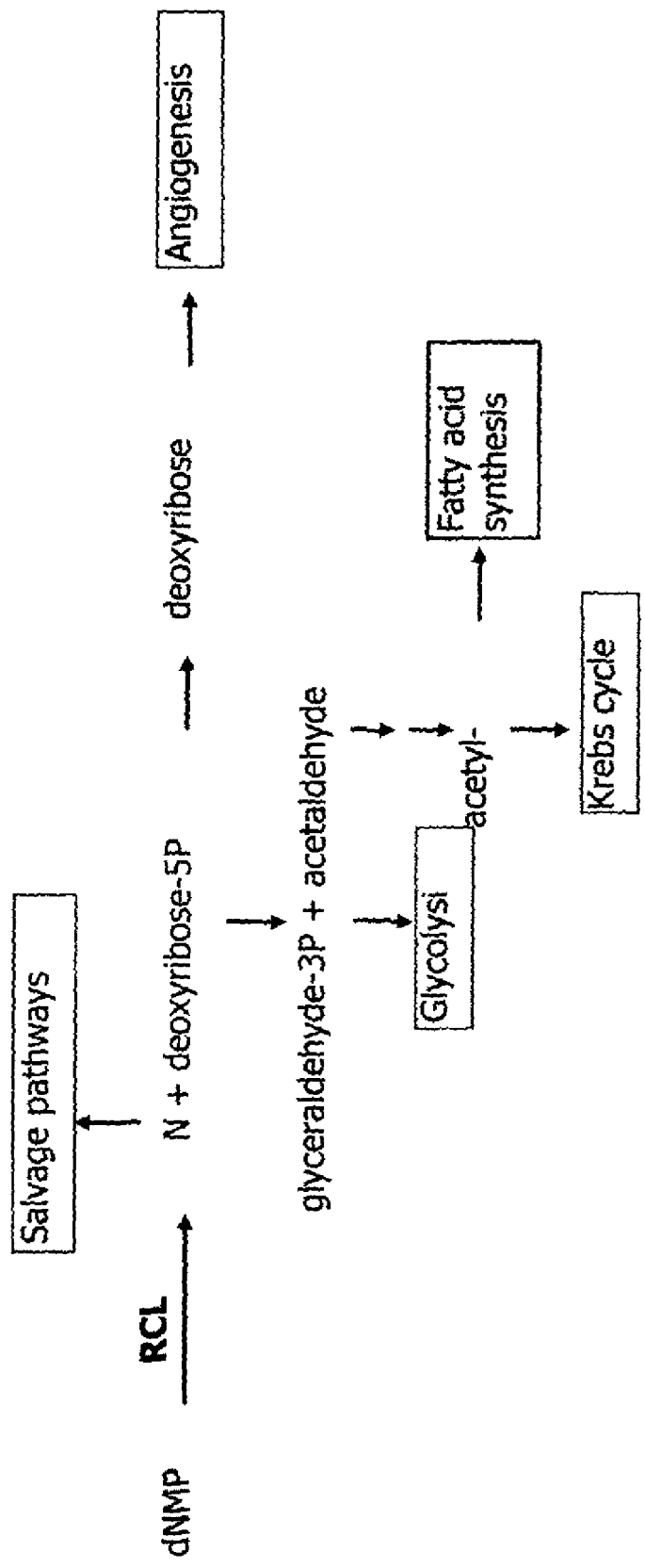
FIG. 5. Possible functional roles of RCL as a previously undescribed deoxynucleoside 5'-monophoshate N-glycosidase. RCL cleaves a deoxynucleoside 5'-monophosphate (dNMP) to liberate the free base N and deoxyribose 5-phosphate. The free base N can be recycled through the purine or pyrimidine salvage pathways. Deoxyribose 5-phosphate can be converted to glyceraldehyde 3-phosphate and acetaldehyde by deoxyribose 5-phosphate aldolase. Glyceraldehyde 3-phosphate can be converted to lactate through glycolysis and acetaldehyde converted to acetyl-CoA by aldehyde oxidase and acetyl-CoA synthetase. Deoxyribose 5-phosphate could be converted to deoxyribose by phosphatase which in turn would stimulate tumor growth and angiogenesis.

RCL has a preference for purine deoxynucleosides 5'-monophosphate, but it remains to be established whether RCL regulates the pool of nucleotides or whether it recognizes modified or anomalous deoxynucleotides. Indeed, the overexpression of RCL could be correlated with the number of anomalous nucleotides found in several types of cancers. The fact that RCL has a low $k_{cat}/K_m$ for all natural deoxynucleotide 5'-monophosphate would support this hypothesis. By regulating the pool of nucleotides, RCL could be a new metabolic enzyme of the purine and pyrimidine salvage pathways. It is well established that the intracellular pool of nucleotides is different under normal and pathological conditions (Traut, T. W. (1994) *Mol Cell Biochem* 140, 1-22). The nucleotide pool is generally elevated in tumor cells by a factor of 5 to 10 as compared to normal cells which can be explained by the fact that tumor cells are actively dividing. Thus, RCL could be involved in the salvage pathway for the reuptake of free bases. Another possibility could be the requirement of supplementary energy for the tumor cells and deoxyribose 5-phosphate could substitute or supplement glucose in aerobic and anaerobic conditions. Indeed, deoxyribose 5-phosphate can be converted by deoxyribose 5-phosphate aldolase into acetaldehyde and glyceraldehyde 3-phosphate that is further catabolized to lactate through glycolysis, while acetaldehyde would be converted into acetyl-CoA (FIG. 5). In addition, deoxyribose 5-phosphate could be dephosphorylated into deoxyribose. Deoxyribose has both chemotactic and angiogenic activity (Akiyama, et al (2004) *Cancer Sci* 95, 851-7). It also inhibits a hypoxia-induced apoptotic pathway. Furthermore, deoxyribose was shown to enhance the level of expression of the angiogenic factor VEGF (Akiyama, et al (2004) *Cancer Sci* 95, 851-7). This could be related to the fact that RCL has transforming activity when coexpressed with VEGF (Lewis, et al (2000) *Cancer Res* 60, 6178-83). Thymidine phosphorylase, which catalyzes the conversion of thymidine to thymine and deoxyribose 1-phosphate, has been known to be angiogenic through deoxyribose and hence is also known as endothelial cell growth factor 1 (ECGF1) (Akiyama, et al (2004) *Cancer Sci* 95, 851-7). In this regard, RCL and thymidine phosphorylase participate in nucleotide metabolism and putatively couple metabolism to intercellular signaling through deoxyribose. In aggregate, the novel catalytic activity of RCL defined here along with the reported activities of the deoxyribose 5-phosphate reveal potential roles for RCL in tumorigenesis. Hence, RCL could be a good target for the development of anti-tumor and or anti-angiogenesis drugs. Further studies of the role in vivo of RCL will contribute to better understand its physiological role in normal and pathological role in cancerous cells.

Example 2

In addition to the studies on RCL (C6orf108) gain-of-function in tumorigenesis, we determined the effect of loss of RCL function on tumorigenesis with the Rat1a-Myc cells. We generated control Rat1a-MYC cells and Rat1a-MYC cells that overexpress the dominant negative Rcl E 93A mutant. Two independent control transfected cell pools and two independent Rcl E 93A Rat1a-MYC transfectant cell pools were studied (FIG. 7).

Figure 7:
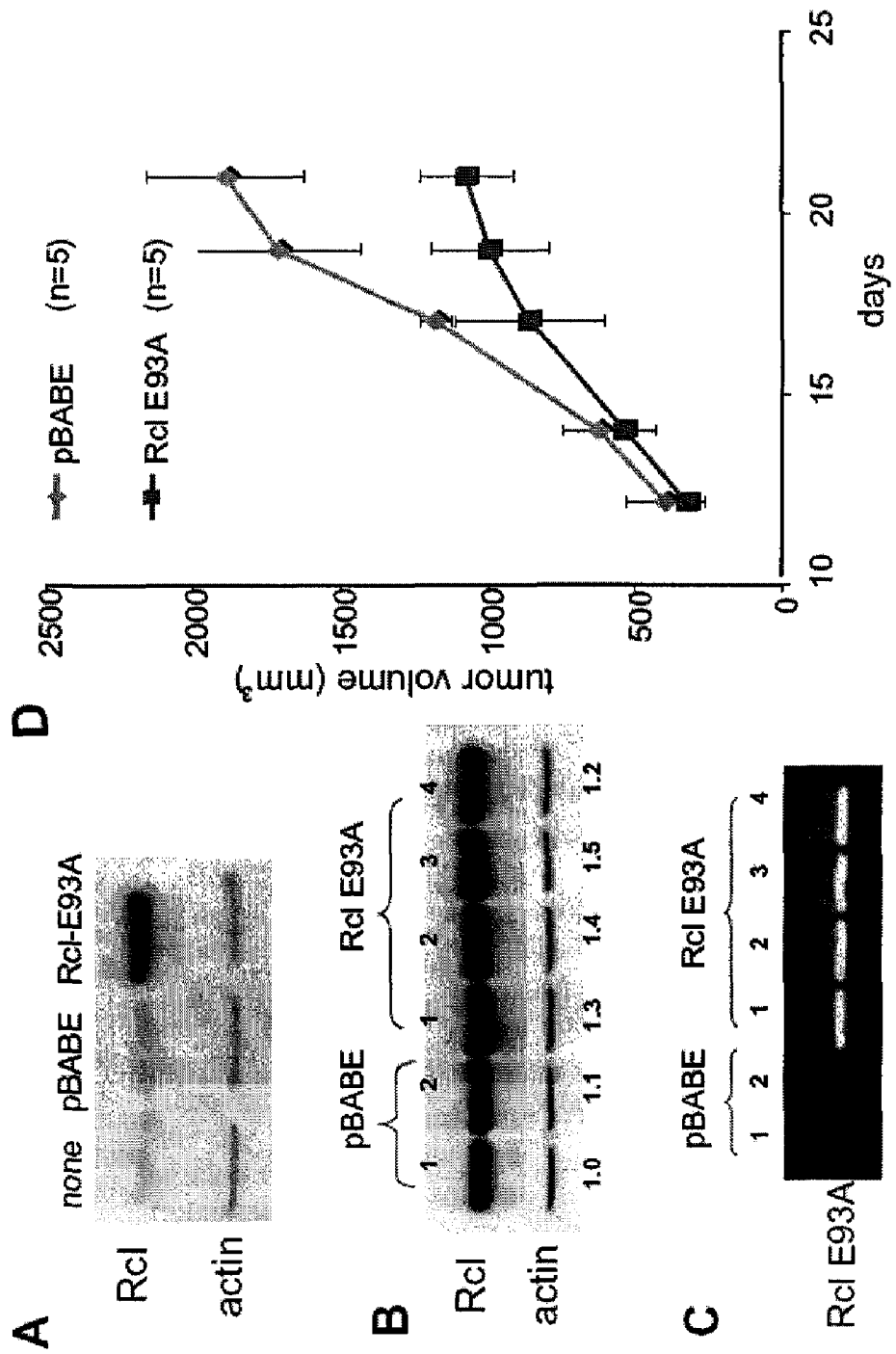
FIG. 7A. Immunoblot showing expression of Rcl-E93A protein in 293T cells; pPURO (pBabe-Puro) represents control transfected cells; none=untransfected cells. B. Immunoblot showing expression of Rcl and Rcl-E 93A in Rat1a-MYC cells (which have high levels of endogenous Rcl). Numbers at the top represents different cell pools. Numbers at the bottom represents normalized relative expression. C. Agarose gel showing expression of Rcl-E93A mRNA in transfectants by RT-PCR of control pPURO or Rcl-E93A expressing Rat1a-MYC cell pools. Signals are dependent on reverse transcriptase (not shown) D. Tumor sizes of pBABE (pools 1 and 2) control Rat1a-Myc cell pools compared with RCL E93A expressing Rat1a-MYC cell pools (E93A#1+E93A#4). Average tumor sizes determined by caliper are shown for groups of nine animals. Error bars are standard deviations.

While the Rcl E 93A mutant does not affect growth rates in vitro, nude mouse xenografts of two independent pools of Rat1a-MYC-Rcl-E93A cells display a remarkable decrease in tumorigenicity as compared with the two control cell pools (FIG. 7). These studies strongly suggest that RCL plays an important role in tumorigenesis, potentially in stressed tumor microenvironment, and that the search for RCL inhibitors is supported by this loss-of-function study.

Obviously, numerous modifications and variations of the present invention are possible in light of the above teachings. It is therefore to be understood that within the scope of the appended claims, the invention may be practiced otherwise than as specifically described herein.

The invention claimed is:

1. A method for identifying a substance with antitumor activity, comprising
  contacting at least one sample comprising an rcl deoxynucleoside 5'-monophosphate N-glycosidase or a cell expressing rcl deoxynucleoside 5'-monophosphate N-glycosidase with the substance;
  measuring the level of enzymatic activity of deoxynucleoside 5'-monophosphate N-glycosidase in the sample;
  comparing the deoxynucleoside 5'-monophosphate N-glycosidase in the sample with at least one control sample comprising an rcl deoxynucleoside 5'-monophosphate N-glycosidase or a cell expressing rcl deoxynucleoside 5'-monophosphate N-glycosidase without the substance;
  selecting the substance which reduces in at least one sample deoxynucleoside 5'-monophosphate N-glycosidase activity compared to a control sample which had not be contacted with the substance;
  administering the selected substance to an animal comprising a tumor;
  evaluating at least one of indicia selected from the group consisting of size of the tumor, growth of the tumor, rate of growth of the tumor, and regression of the tumor; and
  comparing the at least one indicia to an animal also comprising a tumor but to which the selected substance was not administered, wherein a decrease in size and/or decrease in the rate of tumor growth is indicative that the substance has antitumor activity.

2. The method of claim 1, wherein the rcl deoxynucleoside 5'-monophosphate N-glycosidase comprises at least one amino acid sequence selected from the group consisting of SEQ ID NO:6, SEQ ID NO:8, SEQ ID NO:10, SEQ ID NO:24, SEQ ID NO:26, SEQ ID NO:28, SEQ ID NO:30 an amino acid sequence that is 90% identical to SEQ ID NO:6 and which has deoxynucleoside 5'-monophosphate N-glycosidase activity; an amino acid sequence that is 90% identical to SEQ ID NO:8 and which has deoxynucleoside 5'-monophosphate N-glycosidase activity, an amino acid sequence that is 95% identical to SEQ ID NO:6 and which has deoxynucleoside 5'-monophosphate N-glycosidase activity, and an amino acid sequence that is 95% identical to SEQ ID NO:8 and which has deoxynucleoside 5'-monophosphate N-glycosidase activity.

3. The method of claim 2, wherein the rcl deoxynucleoside 5'-monophosphate N-glycosidase comprises SEQ ID NO:6 or an amino acid sequence that is 95% identical to SEQ ID NO:6 and which has deoxynucleoside 5'-monophosphate N-glycosidase activity.

4. The method of claim 2, wherein the rcl deoxynucleoside 5'-monophosphate N-glycosidase comprises SEQ ID NO:8 or an amino acid sequence that is 95% identical to SEQ ID NO:8 and which has deoxynucleoside 5'-monophosphate N-glycosidase activity.

5. The method of claim 2, wherein the rcl deoxynucleoside 5'-monophosphate N-glycosidase comprises SEQ ID NO:10 or an amino acid sequence that is 95% identical to SEQ ID NO:10 and which has deoxynucleoside 5'-monophosphate N-glycosidase activity.

6. The method of claim 1, wherein the sample comprises rcl deoxynucleoside 5'-monophosphate N-glycosidase.

7. The method of claim 1, wherein the sample comprises a cell expressing deoxynucleoside 5'-monophosphate N-glycosidase with the substance.

8. The method of claim 7, wherein the cell comprises an expression vehicle encoding the rcl deoxynucleoside 5'-monophosphate N-glycosidase.

9. The method of claim 8, wherein the expression vehicle comprises at least one nucleotide sequence selected from the group consisting of SEQ ID NO:5, SEQ ID NO:7, SEQ ID NO:9, a nucleotide sequence that is 95% identical to SEQ ID NO:5 and which encodes a protein having deoxynucleoside 5'-monophosphate N-glycosidase activity; a nucleotide sequence that is 95% identical to SEQ ID NO:7 and which encodes a protein having deoxynucleoside 5'-monophosphate N-glycosidase activity, a nucleotide sequence that is 95% identical to SEQ ID NO:9 and which encodes a protein having deoxynucleoside 5'-monophosphate N-glycosidase activity , a nucleotide sequence that hybridizes under stringent conditions to SEQ ID NO:5 and which encodes a protein having deoxynucleoside 5'-monophosphate N-glycosidase activity, and a nucleotide sequence which hybridizes under stringent conditions to SEQ ID NO:7 and which encodes a protein having deoxynucleoside 5'-monophosphate N-glycosidase activity, a nucleotide sequence that hybridizes under stringent conditions to SEQ ID NO:9 and which encodes a protein having deoxynucleoside 5'-monophosphate N-glycosidase activity
  wherein the stringent hybridization conditions comprise hybridization in 50% formamide, 1 M NaCl, 1% SDS at 37° C., and subsequent washing in 0.1×SSC at 60 to 65° C.

10. The method of claim 7, wherein the cell is in an animal.

11. A method for identifying a substance with angiogenesis inhibitory activity, comprising
contacting at least one sample comprising an rcl deoxynucleoside 5'-monophosphate N-glycosidase or a cell expressing rcl deoxynucleoside 5'-monophosphate N-glycosidase with the substance;
measuring the level of deoxynucleoside 5'-monophosphate N-glycosidase enzymatic activity of deoxynucleoside 5'-monophosphate N-glycosidase in the sample;
comparing the deoxynucleoside 5'-monophosphate N-glycosidase in the sample with at least one control sample comprising an rcl deoxynucleoside 5'-monophosphate N-glycosidase or a cell expressing rcl deoxynucleoside 5'-monophosphate N-glycosidase without the substance;
selecting the substance which reduces in at least one sample deoxynucleoside 5'-monophosphate N-glycosidase activity compared to a control sample which had not be contacted with the substance;
testing the selected substance for angiogenesis inhibitory activity.

12. The method of claim 11, wherein the rcl deoxynucleoside 5'-monophosphate N-glycosidase comprises at least one amino acid sequence selected from the group consisting of SEQ ID NO:6, SEQ ID NO:8, SEQ ID NO:10 an amino acid sequence that is 90% identical to SEQ ID NO:6 and which has deoxynucleoside 5'-monophosphate N-glycosidase activity; an amino acid sequence that is 90% identical to SEQ ID NO:8 and which has deoxynucleoside 5'-monophosphate N-glycosidase activity, an amino acid sequence that is 95% identical to SEQ ID NO:6 and which has deoxynucleoside 5'-monophosphate N-glycosidase activity, an amino acid sequence that is 95% identical to SEQ ID NO:8 and which has deoxynucleoside 5'-monophosphate N-glycosidase activity and an amino acid sequence that is 90% identical to SEQ ID NO:10 and which has deoxynucleoside 5'-monophosphate N-glycosidase activity.

13. The method of claim 12, wherein the rcl deoxynucleoside 5'-monophosphate N-glycosidase comprises SEQ ID NO:6 or an amino acid sequence that is 95% identical to SEQ ID NO:6 and which has deoxynucleoside 5'-monophosphate N-glycosidase activity.

14. The method of claim 12, wherein the rcl deoxynucleoside 5'-monophosphate N-glycosidase comprises SEQ ID NO:8 or an amino acid sequence that is 95% identical to SEQ ID NO:8 and which has deoxynucleoside 5'-monophosphate N-glycosidase activity.

15. The method of claim 12, wherein the rcl deoxynucleoside 5'-monophosphate N-glycosidase comprises SEQ ID NO:10 or an amino acid sequence that is 95% identical to SEQ ID NO:10 and which has deoxynucleoside 5'-monophosphate N-glycosidase activity.

16. The method of claim 12, wherein the sample comprises rcl deoxynucleoside 5'-monophosphate N-glycosidase.

17. The method of claim 12, wherein the sample comprises a cell expressing deoxynucleoside 5'-monophosphate N-glycosidase with the substance.

18. The method of claim 17, wherein the cell comprises an expression vehicle encoding the rcl deoxynucleoside 5'-monophosphate N-glycosidase.

19. The method of claim 17, wherein the expression vehicle comprises at least one nucleotide sequence selected from the group consisting of SEQ ID NO:5, SEQ ID NO:7, SEQ ID NO:8, a nucleotide sequence that is 95% identical to SEQ ID NO:5 and which encodes a protein having deoxynucleoside 5'-monophosphate N-glycosidase activity; a nucleotide sequence that is 95% identical to SEQ ID NO:8 and which encodes a protein having deoxynucleoside 5'-monophosphate N-glycosidase activity, a nucleotide sequence that is 95% identical to SEQ ID NO:9 and which encodes a protein having deoxynucleoside 5'-monophosphate N-glycosidase activity, a nucleotide sequence that hybridizes under stringent conditions to SEQ ID NO:5 and which encodes a protein having deoxynucleoside 5'-monophosphate N-glycosidase activity, and a nucleotide sequence which hybridizes under stringent conditions to SEQ ID NO:7, which encodes a protein having deoxynucleoside 5'-monophosphate N-glycosidase activity, and a nucleotide sequence that hybridizes under stringent conditions to SEQ ID NO:9 and which encodes a protein having deoxynucleoside 5'-monophosphate N-glycosidase activity,
wherein the stringent hybridization conditions comprise hybridization in 50% formamide, 1 M NaCl, 1% SDS at 37° C., and subsequent washing in 0.1×SSC at 60 to 65° C.

20. The method of claim 19, wherein the cell is in an animal.

21. The method of claim 12, wherein testing for angiogenesis inhibitory activity comprises comparing vascularization of a tumor in an animal to which the substance has been administered to an animal with a tumor which has not been administered the substance, wherein a decrease in vascularization, rate of vascularization, tumor size, and/or rate of tumor growth indicates that the substance has angiogenesis inhibitory activity.

22. A method for identifying an inhibitor of deoxynucleoside 5'-monophosphate N-glycosidase activity, comprising
contacting at least one sample comprising an rcl deoxynucleoside 5'-monophosphate N-glycosidase or a cell expressing rcl deoxynucleoside 5'-monophosphate N-glycosidase with the substance;
measuring the level of enzymatic activity of deoxynucleoside 5'-monophosphate N-glycosidase in the sample;
comparing the deoxynucleoside 5'-monophosphate N-glycosidase in the sample with at least one control sample comprising an rcl deoxynucleoside 5'-monophosphate N-glycosidase or a cell expressing rcl deoxynucleoside 5'-monophosphate N-glycosidase without the substance;
wherein the substance which reduces in at least one sample deoxynucleoside 5'- to monophosphate N-glycosidase activity compared to a control sample which had not be contacted with the substance is an inhibitor of deoxynucleoside 5'-monophosphate N-glycosidase activity.

23. The method of claim 22, wherein the rcl deoxynucleoside 5'-monophosphate N-glycosidase comprises at least one amino acid sequence selected from the group consisting of SEQ ID NO:6, SEQ ID NO:8, SEQ ID NO:10, an amino acid sequence that is 90% identical to SEQ ID NO:6 and which has deoxynucleoside 5'-monophosphate N-glycosidase activity; an amino acid sequence that is 90% identical to SEQ ID NO:8 and which has deoxynucleoside 5'-monophosphate N-glycosidase activity, an amino acid sequence that is 90% identical to SEQ ID NO:10 and which has deoxynucleoside 5'-monophosphate N-glycosidase activity, an amino acid sequence that is 95% identical to SEQ ID NO:6 and which has deoxynucleoside 5'-monophosphate N-glycosidase activity, an amino acid sequence that is 95% identical to SEQ ID NO:8 and which has deoxynucleoside 5'-monophosphate N-glycosidase activity, and an amino acid sequence that is 95% identical to SEQ ID NO:10 and which has deoxynucleoside 5'-monophosphate N-glycosidase activity.

24. The method of claim 23, wherein the rcl deoxynucleoside 5'-monophosphate N-glycosidase comprises SEQ ID NO:6 or an amino acid sequence that is 95% identical to SEQ ID NO:6 and which has deoxynucleoside 5'-monophosphate N-glycosidase activity.

25. The method of claim 23, wherein the rcl deoxynucleoside 5'-monophosphate N-glycosidase comprises SEQ ID NO:8 or an amino acid sequence that is 95% identical to SEQ ID NO:8 and which has deoxynucleoside 5'-monophosphate N-glycosidase activity.

26. The method of claim 23, wherein the rcl deoxynucleoside 5'-monophosphate N-glycosidase comprises SEQ ID NO:10 or an amino acid sequence that is 95% identical to SEQ ID NO:10 and which has deoxynucleoside 5'-monophosphate N-glycosidase activity.

27. The method of claim 22, wherein the sample comprises rcl deoxynucleoside 5'-monophosphate N-glycosidase.

28. The method of claim 22, wherein the sample comprises a cell expressing deoxynucleoside 5'-monophosphate N-glycosidase with the substance.

29. The method of claim 28, wherein the cell comprises an expression vehicle encoding the rcl deoxynucleoside 5'-monophosphate N-glycosidase.

30. The method of claim 28, wherein the expression vehicle comprises at least one nucleotide sequence selected from the group consisting of SEQ ID NO:5, SEQ ID NO:7, SEQ ID NO:9, a nucleotide sequence that is 95% identical to SEQ ID NO:5 and which encodes a protein having deoxynucleoside 5'-monophosphate N-glycosidase activity; a nucleotide sequence that is 95% identical to SEQ ID NO:8 and which encodes a protein having deoxynucleoside 5'-monophosphate N-glycosidase activity, a nucleotide sequence that is 95% identical to SEQ ID NO:9 and which encodes a protein having deoxynucleoside 5'-monophosphate N-glycosidase activity, a nucleotide sequence that hybridizes under stringent conditions to SEQ ID NO:5 and which encodes a protein having deoxynucleoside 5'-monophosphate N-glycosidase activity, a nucleotide sequence which hybridizes under stringent conditions to SEQ ID NO:7 and which encodes a protein having deoxynucleoside 5'-monophosphate N-glycosidase activity, and a nucleotide sequence that hybridizes under stringent conditions to SEQ ID NO:9 and which encodes a protein having deoxynucleoside 5'-monophosphate N-glycosidase activity, wherein the stringent hybridization conditions comprise hybridization in 50% formamide, 1 M NaCl, 1% SDS at 37° C., and subsequent washing in 0.1×SSC at 60 to 65° C.

31. The method of claim 28, wherein the cell is in an animal.

* * * * *